(12) United States Patent
Sakai

(10) Patent No.: US 7,671,057 B2
(45) Date of Patent: Mar. 2, 2010

(54) THERAPEUTIC AGENT FOR TYPE II DIABETES COMPRISING PROTEASE-INHIBITING COMPOUND

(75) Inventor: Yoshiki Sakai, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 10 days.

(21) Appl. No.: 11/667,099

(22) PCT Filed: Nov. 7, 2005

(86) PCT No.: PCT/JP2005/020380

§ 371 (c)(1),
(2), (4) Date: Jun. 12, 2007

(87) PCT Pub. No.: WO2006/057152

PCT Pub. Date: Jun. 1, 2006

(65) Prior Publication Data

US 2008/0009537 A1    Jan. 10, 2008

(30) Foreign Application Priority Data

Nov. 8, 2004 (JP) ............................. 2004-323188
Apr. 27, 2005 (JP) ............................. 2005-129673

(51) Int. Cl.
 A61K 31/496 (2006.01)
 A61K 31/50 (2006.01)
 A61K 31/445 (2006.01)
 A61K 31/235 (2006.01)
(52) U.S. Cl. ............... 514/255.01; 514/247; 514/331; 514/533; 514/866
(58) Field of Classification Search .......... 514/255.01, 514/247, 331, 533; 515/866
See application file for complete search history.

(56) References Cited

U.S. PATENT DOCUMENTS 5,514,713 A * 5/1996 Nakai et al. .................. 514/533

OTHER PUBLICATIONS

Blakemore et al., "Interleukin-1 receptor antagonist allele (IL1RN*2) associated with nephropathy in diabetes mellitus", Human Genetics, vol. 97, No. 3, pp. 369-374 (1996).*
Y. Sakai, "Shinsei Chinese Hamster ni Okeru Monosodium Glutamate Yuhatsu Tonyobyo ni Taisuru Gosei Trypsin Inhibitor no Yobo Koka Oyobi Chiryo Koka", vol. 27, No. 10, pp. 1083-1093, 1984, (full text), (Abstract).

* cited by examiner

Primary Examiner—Kevin Weddington
(74) Attorney, Agent, or Firm—Wenderoth, Lind & Ponack, L.L.P.

(57) ABSTRACT

The problem of the present invention is to provide a preventive and/or therapeutic agent for diabetes and/or complications of diabetes based on the novel mode of action.

The protease-inhibiting compound according to the present invention is a compound represented by the general formula (I)

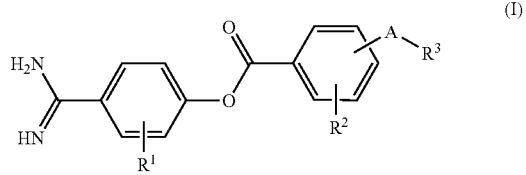

[wherein all the symbols have the same meanings as described in the specification], its salt or solvate, or a prodrug thereof, is useful as a preventive and/or therapeutic agent for diabetes and/or complications of diabetes.

10 Claims, 1 Drawing Sheet

THERAPEUTIC AGENT FOR TYPE II DIABETES COMPRISING PROTEASE-INHIBITING COMPOUND

This application is a U.S. national stage of International Application No. PCT/JP2005/020380 filed Nov. 7, 2005.

TECHNICAL FIELD

The present invention relates to a preventive and/or therapeutic agent for diabetes and/or complications of diabetes which comprises a protease-inhibiting compound.

In more detail, the present invention relates to a preventive and/or therapeutic agent for diabetes and/or complications of diabetes which comprises a protease-inhibiting compound, in particular, a compound represented by the general formula (I)

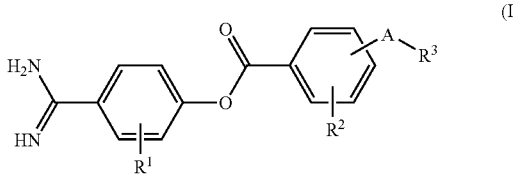

(wherein all the symbols have the same meanings as described below), its salt or solvate, or a prodrug thereof.

BACKGROUND ART

Recently, the treatment through administration of insulin preparations has been performed mainly for patients with severe diabetes. Various insulin preparations aiming at improving the patients' QOL, such as quick-acting or sustained-release subcutaneous preparations, inhalers, oral preparations and the like have been developed, but they are by far inferior to the physiologic function of the pancreatic beta cells that act to accomplish automatic or autonomic fine adjustment according as the blood sugar level varies. Additionally, the long-term administration results in eventual onset of complications of diabetes (microangiopathy and large-vessel disorders), which constitute a major risk factor for arteriosclerosis.

Insulin is the most important blood-sugar regulating hormone in animals and its production or generation and secretion are locally limited to the pancreatic beta cells. Therefore, the research and development work, which is currently under way on the diabetic drugs, includes (1) the research on the development, differentiation, apoptosis and regeneration of the pancreatic beta cells, (2) the research on the insulin secretion mechanism, (3) the research on deficiency of the action of insulin and the like.

The pancreatic beta cells, though they were once considered non-proliferative, continue to undergo new regeneration from their precursor cells to form the islet cells even after birth, according as various environmental factors change. In addition, the differentiated pancreatic beta cells are known to proliferate but at a low rate. On the other hand, part of the pancreatic beta cells is lost by apoptosis and turns over every 40 to 50 days. In these manners, it has been clarified that the amount or quantity of the pancreatic beta cells gently increases throughout their lives.

Insulin resistance develops by damages to the cells, as well as pregnancy, obesity and the like, and in the case of an increased requirement of insulin secretion, new beta cells regenerate from their precursor cells being accompanied by beta cell hypertrophy. As a result, the amount or quantity of the beta cells increases, and normal sugar metabolism is maintained.

Insulin secretagogues represented by sulfonylurea drug agents, on the other hand, exhaust the pancreatic beta cells eventually.

Referring to an approach from the standpoint of regenerative medicine, enhanced attention as a novel remedy for diabetes is being drawn to a method which involves activating in vivo the differentiation-inducing system of endogenous precursor (stem) cells of the pancreatic beta cells to thereby promote proliferation of the pancreatic beta cells for enhancement of their function. From the research study on the human embryonic pancreatic cells utilized for the differentiation/proliferation and function-enhancement actions for the pancreatic beta cells, notice has also been attracted to the cytokines of various growth factors, such as HGF (hepatocyte growth factor) and the like, and many reports have recently been published. In addition, attention is being directed to the remedy concerning the management of glucagon-like peptide-1 (hereinafter abbreviated as GLP-1) and gastric inhibitory peptide (hereinafter abbreviated as GIP), which are the gastrointestinal hormones possessing the same action.

GLP-1 and GIP, belonging to a group of gut-derived hormones called incretins, are the peptides that are profoundly involved in the adjustment or regulation of the glucose homeostasis. GLP-1 is synthesized in gut L cells through tissue-specific posttranslational processing of a preproglucagon, or a glucagon precursor, and is released into the circulation in response to a diet. These peptides are major mediators of the enteroinsular axis and bind to specific receptors to exert their actions.

GLP-1 acts mainly on the pancreas and is known to promote the insulin release by pancreatic beta cells in a glucose-concentration dependent manner. Additionally, GLP-1 inhibits glucagon secretion and delays emptying of stomach, and there is suggested a possibility that it would augment peripheral glucose disposal through metabolism.

From the fact that postcibal glucose levels are normalized in patients with noninsulin-dependent diabetes mellitus by administration of GLP-1, the possibility is suggested that GLP-1 could be used as a therapeutic drug for diabetes mellitus (refer to Diabetes care, 17(9), pp. 1039-1044, (1994)). Also, GLP-1 displays the blood-sugar controlling action in patients with insulin-dependent diabetes mellitus (refer to Diabetes Care, 19(6), pp. 580-586, (1996)). Since the insulin-release promoting action of GLP-1 depends on the plasma glucose levels (refer to Nature, 361, pp. 362-265, (1993)), furthermore, the insulin release mediated by GLP-1 is reduced at lowered plasma glucose levels, thereby offering the advantages that severe hypoglycemia is not induced and that body weight gain is not promoted. Consequently, diabetes treatment with an enhanced degree of safety can be considered feasible by controlling the blood GLP-1 levels, as the case may be.

As a procedure of controlling the plasma GLP-1 levels, it is possible to administer to patients GLP-1 itself or modified GLP-1, but activated GLP-1 (GLP-1[7-36]amide), which shows a very short plasma half-life of about 1 to 6 minutes and turns into inactivated GLP-1 (GLP-1[9-36]amide) (refer to Endocrinology, 136, pp. 3585-3596, (1995)), can offer the limited possibility as a therapeutic agent. As a stable modified GLP-1 agonist, in addition, exendin-4 and others have been developed, but these are required to be injected twice a day, while their side effects, such as emesis, have been reported.

Furthermore, the inactivation of activated GLP-1 by dipeptidyl-peptidase IV (hereinafter referred to briefly as DPP-IV) is known as a mechanism for controlling the plasma GLP-1 level. Accordingly, it is possible to maintain the required amount of activated GLP-1 in blood by inhibiting DPP-IV (refer to Diabetologia, 42, pp. 1324-1331, (1999)), and Diabetes 47, pp. 1663-1670, (1998)).

Also, there have been published the compounds that generate or induce the secretion of GLP-1 (refer to WO99/08991, 41st Annual Meeting of the Japan Diabetes Society, No. 3N 004, (1998), and 43rd Annual Meeting of the Japan Diabetes Society, No. I-5-12 (2000)).

The protease-inhibiting compounds, as described in JP-A 52-89640, have been demonstrated to inhibit onset of diabetes-like symptoms in diabetes animal models, and have also been reported to exhibit suppression of fasting blood sugar levels, retention or maintenance of pancreatic insulin generation or secretion, and suppression of plasma glucagon amount and glucagon content (refer to Journal of the Japan Diabetes Society, 24(1), pp. 77-79, (1981), Journal of the Japan Diabetes Society, 27(10), pp. 1083-1093, (1984), Endocrine Journal (the Japan Endocrine Society) 60(5), pp. 684-695, (1984), and Pancreas 8(2), pp. 196-203, (1993)). In addition, said compounds have been proven to promote significant decreases in blood sugar levels and also eventual reduction of insulin requirements in patients with noninsulin-dependent diabetes mellitus, while the possibility of ameliorating abnormal glucagon secretion is suggested (refer to New Horizon for Medicine, 21, pp. 2806-2810, (1989)).

Meanwhile, the protease-inhibiting compounds according to the present invention are described in JP-A H08-109164, JP-A H07-206801, JP-A H08-143529, JP-A S61-33173 and Biochemica Biophysica Acta, 661(2), pp. 342 (1981), however, it is not suggested that these compounds exhibit such actions as suppression of fasting blood sugar levels, retention or maintenance of pancreatic insulin generation or secretion, suppression of plasma glucagon amounts, promotion of GLP-1 increases and inhibition of complications of diabetes and the like.

DISCLOSURE OF THE INVENTION

The Problem to Be Solved by the Invention

If there can be found out any compounds exhibiting the actions to depress and/or reduce elevations in blood sugar levels, they are useful as a preventive and/or therapeutic agent for diabetes and/or complications of diabetes, and discovery of such compounds is demanded.

Means to Solve the Problem

The present inventors, with a specific view to finding out a compound exhibiting the actions to suppress and/or reduce elevations in blood sugar levels, conducted intensive investigation, and as a result, found that the protease-inhibiting compounds according to the present invention can solve such problem, leading to completion of the present invention.

Thus, the present invention relates to:
(1) A preventive and/or therapeutic agent for diabetes and/or complications of diabetes which comprises a protease-inhibiting compound;
(2) The agent as described above under (1), wherein the protease-inhibiting compound is a serine protease-inhibiting compound;
(3) The agent as described above under (1), wherein the protease-inhibiting compound is a compound represented by the general formula (I):

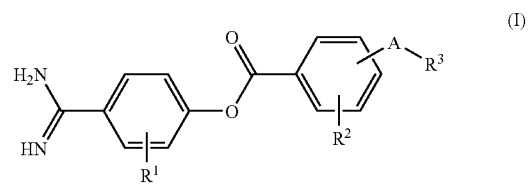

[wherein $R^1$ and $R^2$ each independently are a hydrogen atom, a C1-4 alkyl, C1-4 alkoxy or C2-5 acyl group, a halogen atom, a nitro or benzoyl group, or $COOR^4$ (where $R^4$ is a C1-3 alkyl group); A is a single bond, a C1-4 alkylene group, or a group represented by the formula:

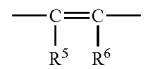

(wherein, $R^5$ and $R^6$ each independently are a hydrogen atom or a C1-4 alkyl group); $R^3$ is a group represented by the general formula:

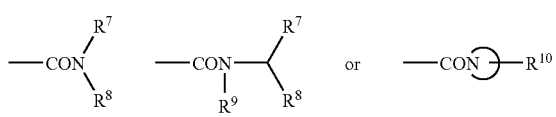

(wherein $R^7$ and $R^8$ are each independently (1) a hydrogen atom, (2) a phenyl group, (3) a C7-10 phenylalkyl group, (4) a phenyl group substituted by one or more substituents selected from a C1-4 alkyl group, a halogen atom and —$R^{11}$—$COOR^{12}$ (where $R^{11}$ is a single bond, a C1-8 alkylene, C2-8 alkenylene or C2-8 alkynylene group; $R^{12}$ is a hydrogen atom, a C1-4 alkyl, C7-10 phenylalkyl, phenyl, aryl or propargyl group) or a C7-10 phenylalkyl group, (5) a C1-10 alkyl group, (6) a C2-10 alkenyl group having 1 to 3 double bonds, (7) a C2-10 alkynyl group having 1 to 2 triple bonds, (8) —$R^{11a}$—$COXR^{12}$ (where $R^{11a}$ is a single bond, a C1-8 alkylene group, a C2-8 alkylene group having one or two carbon atoms in the principal chain substituted by a sulfur atom or a sulfur atom and a phenylene group, a C2-8 alkenylene group, a C4-8 alkenylene group having one or two carbon atoms in the principal chain substituted by a sulfur atom, or a sulfur atom and a phenylene group, a C2-8 alkynylene group, or a C4-8 alkynylene group having one or two carbon atoms in the principal chain substituted by a sulfur atom or a sulfur atom and a phenylene group; X is an oxygen atom or NH; $R^{12}$ has the same meaning as described above), (9) a C1-4 alkyl group substituted by a 7-14 membered, bi- or tri-cyclic hetero ring containing one nitrogen atom, (10) a C3-7 cycloalkyl group or (11) a C1-6 alkyl group substituted by a C1-4 alkoxy group; $R^9$ is (1) a hydrogen atom, (2) a C1-8 alkyl group, (3) a C7-10 phenylalkyl group, (4) a C2-10 alkenyl group having 1 to 3 double bonds, (5) a C2-10 alkynyl group having 1 to 2 triple bonds, (6) —$R^{11}$—$COOR^{12}$ (where $R^{11}$ and $R^{12}$ have the same meaning as described above), (7) a C3-7 cycloalkyl group, or (8) a C1-6 alkyl group substituted by a C1-4 alkoxy group; the symbol:

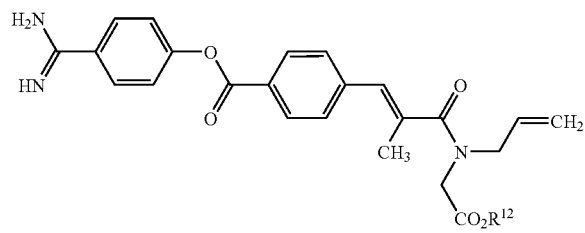

is a 4-7 membered, mono-cyclic hetero ring containing one or two nitrogen atoms; $R^{10}$ is (1) a hydrogen atom, (2) a C7-10 phenylalkyl group, or (3) $COOR^{13}$ (wherein, $R^{13}$ is a hydrogen atom, C1-4 alkyl or C7-10 phenylalkyl)), with the proviso that $R^7$ and $R^8$ shall not be understood to represent hydrogen atom at the same time and, when at least one group of $R^7$, $R^8$ and $R^9$ represents a group containing t-butyl ester, the other groups shall not be understood to represent a group containing carboxyl], its salt or solvate, or a prodrug thereof;

(4) The agent as described above under (3), wherein the compound represented by the general formula (I) is a compound represented by the formula:

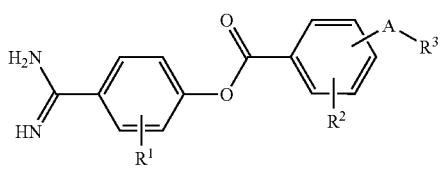

(I-1)

(wherein $R^{12}$ is a hydrogen atom or a C1-4 alkyl group);

(5) The agent as described above under (4), wherein $R^{12}$ is a hydrogen atom or an ethyl group;

(6) The agent as described above under (3), which is a GLP-1 generation enhancer;

(7) The agent as described above under (3) or (6), which is a glucagon amount inhibitor;

(8) The agent as described above under (3) or (6), which is a blood-sugar elevation suppressor and/or blood-sugar lowering agent;

(9) The agent as described above under (3) or (7), which is a lipid-lowering agent;

(10) The agent as described above under (3), which is a pancreatic beta-cell regeneration promoter;

(11) The agent as described above under (3), (6) or (10), which is insulin-synthesis promoter;

(12) The agent as described above under (1), wherein diabetes is non-insulin-dependent diabetes mellitus or insulin-dependent diabetes mellitus;

(13) A preventive and/or therapeutic agent for arteriosclerosis, wherein the protease-inhibiting compound is a compound represented by the general formula (I):

(I)

[wherein all the symbols have the same meanings as described above under (3)], its salt or solvate, or a prodrug thereof;

(14) A pharmaceutical composition which comprises a combination of the compound represented by the general formula (I) as described above under (3), its salt or solvate, or a prodrug thereof with one or more kinds selected from the aldose reductase inhibitor, insulin preparation, insulin secretagogue, fast insulin secretagogue, sulfonylurea drug, biguanide drug, GLP-1 analogue, DPP-IV inhibitor, a-glycosylase inhibitor, glucagon antagonist, PPAR (peroxisome proliferator-activated receptor) agonist, PPAR-γ agonist, PPAR-a agonist, PPAR-α and -γ agonists, fructose-bisphosphatase inhibitor, GSK-3B (glycogen synthase kinase 3B) inhibitor, low affinity sodium/glucose cotransporter inhibitor, Glut4 (glucose transporter-4) transport promoter, phosphatidyl inositol stimulator, phosphatase inhibitor, prostaglandin synthesis stimulator, trypsin phosphatase inhibitor, hydroxysteroid dehydrogenase inhibitor, carnitine palmitoyltransferase inhibitor, lipase inhibitor, lipid peroxidative inhibitor, dopamine D2 agonist, β3 agonist, amylin agonist, histamine H1 antagonist, sodium channel antagonist, adenosine A2 agonist, potassium channel opener, antioxidant drug, 5-HT (serotonin) uptake inhibitor, 5-HT2C agonist, TNF-a (Tumor Necrosis Factor-a) antagonist, anti CD3 monoclonal antibody, anti GDF-8 (growth/differentiation factor-8) antibody, IL-2 agonist, recombinant human IGF-1 (insulin-like growth factor-1), somatostatin agonist, PKC (proteinase kinase C) inhibitor, NGF (nerve growth factor) agonist, EGF (epidermal growth factor) agonist, PDGF (platelet-derived growth factor) agonist, immunosuppressive drug, and remedy for complications of diabetes;

(15) A pharmaceutical composition which comprises a combination of the compound represented by the general formula (I) as described above under (3), its salt or solvate, or a prodrug thereof with one or more kinds selected from the hypotensive drug, diuretic drug, antihyperlipidemic drug, circulation improving drug, remedy for stroke, remedy for renal disease, remedy for pancreatic disease, antiplatelet drug, anti-arteriosclerotic drug and anti-inflammatory drug;

(16) A use of the compound represented by the general formula (I) as described above under (3), its salt or solvate, or a prodrug thereof for preparing a preventive and/or therapeutic agent for diabetes and/or complications of diabetes,

(17) A method for prevention and/or treatment for diabetes and/or complications of diabetes, characterized in that said method comprises administering a mammal an effective dose of the compound represented by the general formula (I) as described above under (3), its salt or solvate, or a prodrug thereof;

(18) A use of the compound represented by the general formula (I) as described above under (3), its salt or solvate, or a prodrug thereof for preparing a GLP-1 generation enhancer;

(19) A method for enhancing GLP-1 generation, characterized in that said method comprises administering a mammal an effective dose of the compound represented by the general formula (I) as described above under (3), its salt or solvate, or a prodrug thereof to;

(20) A use of the compound represented by the general formula (I) as described above under (3), its salt or solvate, or a prodrug thereof for preparing a glucagon amount inhibitor;

(21) A method for inhibiting a glucagon amount, characterized in that said method comprises administering a mammal an effective dose of the compound represented by the general formula (I) as described above under (3), its salt or solvate, or a prodrug thereof;

(22) A use of the compound represented by the general formula (I) as described above under (3), its salt or solvate, or a prodrug thereof for preparing a blood-sugar elevation suppressor and/or blood-sugar lowering agent;

(23) A method for suppressing the blood-sugar elevation and/or lowering the blood-sugar, characterized in that said method comprises administering a mammal an effective dose of the compound represented by the general formula (I) as described above under (3), its salt or solvate, or a prodrug thereof;

(24) A use of the compound represented by the general formula (I) as described above under (3), its salt or solvate, or a prodrug thereof for preparing a lipid lowering agent;

(25) A method for lowering lipid is characterized in that said method comprises administering an effective dose of the compound represented by the general formula (I) as described above under (3), its salt or solvate, or a prodrug thereof to a mammal;

(26) A use of the compound represented by the general formula (I) as described above under (3), its salt or solvate, or a prodrug thereof for preparing a pancreatic beta-cell regeneration promoter;

(27) A method for promoting the pancreatic beta-cell regeneration, characterized in that said method comprises administering a mammal an effective dose of the compound represented by the general formula (I) as described above under (3), its salt or solvate, or a prodrug thereof;

(28) A use of the compound represented by the general formula (I) as described above under (3), its salt or solvate, or a prodrug thereof for preparing an insulin synthetic promoter;

(29) A method for promoting the insulin synthesis, characterized in that said method comprises administering a mammal an effective dose of the compound represented by the general formula (I) as described above under (3), its salt or solvate, or a prodrug thereof;

(30) A use of the compound represented by the general formula (I) as described above under (3), its salt or solvate, or a prodrug thereof for preparing a preventive and/or therapeutic agent for arteriosclerosis;

(31) A method for preventing and/or treating arteriosclerosis is characterized in that said method comprises administering a mammal an effective dose of the compound represented by the general formula (I) as described above under (3), its salt or solvate, or a prodrug thereof;

(32) The agent as described above under (1), wherein the protease-inhibiting compound is 6-amidino-2-naphthyl p-guanidinobenzoate or 6-amidino-2-naphthyl 4-[(4,5)-dihydro-1H-imidazol-2-yl)amino]benzoate, its salt or solvate, or a prodrug thereof; and

(33) The agent as described above under (4), wherein the compound represented by the general formula (I) is N-allyl-N—[(E)-2-methyl-3-[4-(4-amidinophenoxycarbonyl)-phenyl]-propenoyl]amino acetate or N-allyl-N-{(2E)-3-[4-({4-[amino(imino)methyl]phenoxy}carbon yl)-phenyl]-2-methyl-2-propenoyl}glycine, its salt or solvate, or a prodrug thereof.

EFFECT OF THE INVENTION

Since the protease-inhibiting compounds according to the present invention exhibit the GLP-1 generation enhancing action, glucagon amount inhibiting action, blood-sugar elevation suppressing and/or blood-sugar lowering action, blood-lipid suppressing and/or blood-lipid lowering action and insulin-synthesis promoting action, they can be used as a preventive and/or therapeutic agent for diabetes and/or complications of diabetes.

BEST MODE OF THE CARRYING OUT THE INVENTION

Figure 1:
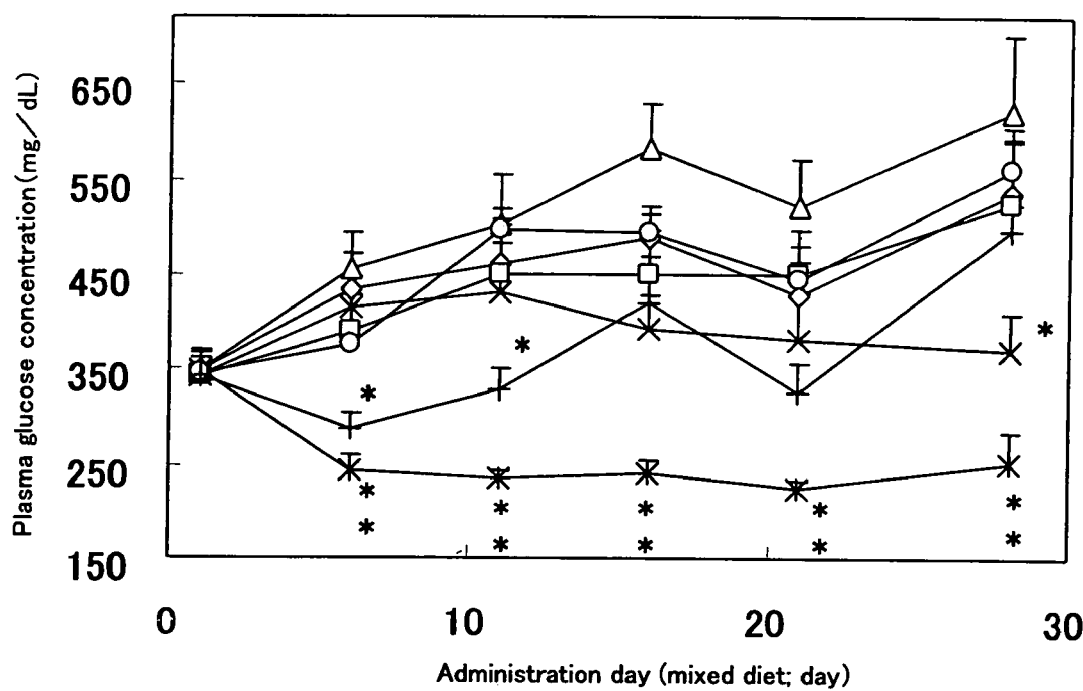
FIG. 1 is a FIGURE showing time-course changes (**: $P<0.01$ vs. control group, *: $P<0.05$ vs. control group) of the blood-sugar lowering action in KK-$A^y$/Ta mouse of the compounds according to the present invention.

In the specification (or As used herein), the C1-3 alkyl group may be exemplified by methyl, ethyl, propyl and isopropyl groups.

In the specification, the C1-4 alkyl group may be exemplified by methyl, ethyl, propyl, isopropyl, butyl, isobutyl, sec-butyl and tert-butyl groups.

In the specification, the C1-6 alkyl group may be exemplified by straight-chain and branched alkyl groups, such as methyl, ethyl, propyl, butyl, isobutyl, sec-butyl, tert-butyl, pentyl and hexyl groups, etc.

In the specification, the C1-8 alkyl group may be exemplified by straight-chain and branched alkyl such as, methyl, ethyl, propyl, butyl, isobutyl, sec-butyl, tert-butyl, pentyl, hexyl, heptyl, octyl and the like.

In the specification, the C1-10 alkyl group may be exemplified by straight-chain and branched alkyl groups, such as methyl, ethyl, propyl, isopropyl, butyl, isobutyl, sec-butyl, tert-butyl, pentyl, hexyl, heptyl, octyl, nonyl and decyl groups, etc.

In the specification, the C7-10 phenylalkyl group may be exemplified by straight-chain and branched alkyl groups, such as methyl, ethyl, propyl and butyl groups which are substituted by one phenyl group.

In the specification, the C2-10 alkenyl group may be exemplified by straight-chain and branched alkenyl groups, such as vinyl, propenyl (e.g. acryl or 2-propenyl), butenyl, pentenyl, hexenyl, heptenyl, octenyl, nonenyl, decenyl, undecenyl and dodecenyl groups, etc.

In the specification, the alkoxy group may be exemplified by methoxy, ethoxy, propoxy, isopropoxy, butoxy, isobutoxy, sec-butoxy and tert-butoxy groups, etc.

In the specification, the C1-10 alkoxy group may be exemplified by straight-chain and branched alkoxy groups, such as methoxy, ethoxy, propoxy, isopropoxy, butoxy, isobutoxy, sec-butoxy, tert-butoxy, pentyloxy, isopentyloxy, neopentyloxy, hexyloxy, isohexyloxy, heptyloxy, octyloxy, nonyloxy and decyloxy groups, etc.

In the specification, the C2-5 acyl group may be exemplified by straight-chain and branched acyl groups, such as ethanoyl, propanoyl, butanoyl, 2-methylpropanoyl, pentanoyl, 2-methylbutanoyl and 3-methylbutanoyl groups, etc.

In the specification, the halogen atom may be exemplified by fluorine, chlorine, bromine and iodine atoms.

In the specification, the trihalomethyl group means a methyl group being substituted by three halogen atoms. Specifically, it may be exemplified by trifluoromethyl, trichloromethyl and tributylmethyl groups.

In the specification, the C1-4 alkylene group may be exemplified by methylene, ethylene, propylene, isopropylene, butylenes and isobutylene groups, etc.

In the specification, the C1-8 alkylene group may be exemplified by straight-chain and branched alkylene groups, suchasmethylene, ethylene, propylene, isopropylene, butylene, isobutylene, pentamethylene, hexamethylene, heptamethylene and octamethylene groups, etc.

In the specification, the C2-8 alkylene group means straight-chain and branched alkylene groups, such as ethylene, propylene, isopropylene, butylenes, isobutylene, pentamethylene, hexamethylene, heptamethylene and octamethylene groups, etc.

In the specification, the C2-8 alkenylene group may be exemplified by straight-chain and branched alkenylene groups, such as vinylene, propenylene, 1-, or 2-butenylene, butadienylene, pentenylene, hexenylene, heptenylene and octenylene groups, etc.

In the specification, the C2-8 alkynylene group may be exemplified by straight-chain and branched alkynylene groups, such as ethynylene, 1-, or 2-propynylene, 1-, or 2-butynylene, pentynylene, hexynylene, heptynylene and octynylene groups, etc.

In the specification, the C2-8 alkylene group in which one or two carbon atoms in the principal chain are substituted by a sulfur atom, or a sulfur atom and a phenylene group may be exemplified by thiaethylene (which represents the formulae, —CH$_2$—S— and —S—CH$_2$—), thiatrimethylene (which represents the formulae, —CH$_2$—CH$_2$—S—, —CH$_2$—S—CH$_2$— and —S—CH$_2$—CH$_2$—), thiatetramethylene, thiapentamethylene, thiahexamethylene, thiaheptamethylene, thiaoctamethylene and isomers thereof, or these methylene groups of which either one is substituted by a phenylene group (e.g. —CH$_2$—S—CH$_2$—C$_6$H$_4$—, etc.). In the specification, the C4-8 alkenylene group in which one or two carbon atoms in the principal chain are substituted by sulfur, or sulfur and phenylene means thiabutenylene (which represents the formulae, —S—CH$_2$—CH=CH—, —CH=CH—CH$_2$—S—), thiapentenylene (which represents the formulae, —S—CH$_2$—CH$_2$—CH=CH—, —S—CH$_2$—CH=CH—CH$_2$—, —CH$_2$—S—CH$_2$—CH=CH—), thiahexenylene, thiaheptenylene, thiaoctenylene and isomers thereof, or these methylene groups of which either one is substituted by a phenylene group (e.g. —S—CH$_2$—CH=CH—C$_6$H$_4$—, etc.).

In the specification, the C4-8 alkynylene in which one or two carbon atoms in the principal chain are substituted by a sulfur atom or a sulfur atom and a phenylene group may be exemplified by thiabutynylene (which represents the formulae, —S—CH$_2$—C≡C—, —C≡C—CH$_2$—S—), thiapentynylene (which represents the formulae, —S—CH$_2$—CH$_2$—C≡C—, —C≡C—CH$_2$—CH$_2$—S—, —S—CH$_2$—C≡C—CH$_2$—, —CH$_2$—C≡C—CH$_2$—S—, —CH$_2$—S—CH$_2$—C≡C—, —C≡C—CH$_2$—S—CH$_2$—), thiahexynylene, thiaheptynylene, thiaoctynylene and isomers thereof, or these methylene groups of which either one is substituted byaphenylene group (e.g. —S—CH$_2$—C≡C—C$_6$H$_4$—, etc.). In the specification, the 7-14 membered, bi- or tri-cyclic hetero ring containing one nitrogen atom may be exemplified by indole, indoline, quinoline, 1,2,3,4-tetrahydroquinoline and carbazole rings, etc.

In the specification, the C2-10 alkenyl group having 1 to 3 double bonds may be exemplified by vinyl, propenyl (e.g. allyl or 2-propenyl), butenyl, pentenyl, hexenyl, heptenyl, octenyl, nonenyl, decenyl, butadienyl, pentadienyl, hexadienyl, heptadienyl, octadienyl, nonanidenyl, decadienyl, hexatrienyl, heptatrienyl, octatrienyl, nonatrienyl and decatrienyl groups, etc. and isomers thereof.

In the specification, the C2-10 alkynyl group having 1 to 2 triple bonds is exemplified by ethynyl, propynyl, butynyl, pentynyl, hexynyl, heptynyl, octynyl, nonynyl, decynyl, butadiynyl, pentadiynyl, hexadiynyl, heptadiynyl, octadiynyl, nonadiynyl and decadiynyl groups, etc. and isomers thereof.

In the specification, the C3-7 cycloalkyl group may be exemplified by cyclopropyl, cyclobutyl, cyclopentyl, cyclohexyl and cycloheptyl groups, etc.

In the formula (I), the 4-7 membered mono-cyclic hetero ring containing one or two nitrogen atoms represented by the symbol:

may be exemplified by pyrrole, pyrrolidine, imidazole, imidazolidine, pyridine, piperidine, pyrazine, piperazine and pyrimidine rings, etc.

In the specification, the protease-inhibiting compound may be exemplified by serine protease-inhibiting compounds, such as trypsin-inhibiting compounds, chymotripsin-inhibiting compounds and the like, with the trypsin-inhibiting compounds being preferable.

In the specification, the serine protease-inhibiting compound may be exemplified by the compounds described in JP-A S52-89640, JP-A H08-109164, JP-A H07-206801, JP-A H08-143529 and JP-A S61-33173, their salts and solvates, and prodrugs thereof. The compounds according to the present invention and the compounds to be indicated in Examples are named and termed by using the software package, ACD/Name (version 6.00, Advanced Chemistry Development Inc.). The preferable ones among these compounds include the compounds represented by the general formula (I), or 6-amidino-2-naphthyl p-guanidinobenzoate, 6-amidino-2-naphthyl 4-[(4,5)-dihydro-1H-imidazol-2-yl)amino] benzoate and N,N-dimethylcarbamoylmethyl 4-(4-guanidinobenzoyloxy)phenylacetate, their salts and solvates, and prodrugs thereof.

In the present invention, the specific compounds represented by the general formula (I) may be exemplified by 4-[amino(imino)methyl]phenyl 4-([(2-ethoxy-2-oxoethyl)(phenyl)amino]carbonyl)benzoate, 4-[amino(imino)methyl]phenyl 4-{(1E)-3-[(2-ethoxy-2-oxoethyl)(phenyl)amino]-3-oxo-1-propenyl}benzoate, ethyl N-[4-({4-[amino(imino)methyl]phenoxy}carbonyl)benzoyl]tryptophanate, ethyl 1-[4-({4-[amino(imino)methyl]phenoxy}carbonyl)benzoyl]-L-prolinate, ethyl 1-[4-({4-[amino(imino)methyl]phenoxy}carbonyl)benzoyl]-D-prolinate, benzyl 1-[4-({4-[amino(imino)methyl]phenoxy}carbonyl)benzoyl]-D-prolinate, 4-[amino(imino)methyl]phenyl 4-{[benzyl(2-ethoxy-2-oxoethyl)amino]carbonyl}benzoate, 4-[amino(imino)methyl]phenyl 4-{(1E)-3-[(2-ethoxy-2-oxoethyl)(phenyl)amino]-2-methyl-3-oxo-1-propenyl}benzoate, ethyl 1-{(2E)-3-[4-({4-[amino(imino)methyl]phenoxy}carbonyl)phenyl]-2-propenoyl}-L-prolinate, ethyl 1-{(2E)-3-[4-({4-[amino(imino)methyl]phenoxy}carbonyl)phenyl]-2-propenoyl}-D-prolinate, methyl 5-[amino(imino)methyl]-2-[(4-{[(2-ethoxy-2-oxoethyl)(phenyl)amino]carbonyl}benzoyl)oxy]benzoate, 4-[amino(imino)methyl]phenyl 4-{(1E)-3-[(2-ethoxy-2-oxoethyl)(phenyl)amino]-1-methyl-3-oxo-1-propenyl}benzoate, 4-[amino(imino)methyl]phenyl 4-{(1E)-3-[benzyl(2-ethoxy-2-oxoethyl)amino]-2-methyl-3-oxo-1-propenyl}benzoate, ethyl N-{(2E)-3-[4-({4-[amino(imino)methyl]phenoxy}carbonyl)phenyl]-2-methyl-2-propenoyl}-L-phenylalaninate, ethyl N-{(2E)-3-[4-({4-[amino(imino)methyl]phenoxy}carbonyl)phenyl]-2-methyl-2-propenoyl}-L-triptophanate, benzyl 1-{(2E)-3-[4-({4-

(amino(imino)methyl]phenoxy}carbonyl)phenyl]-2-methyl-2-propenoyl}-L-prolinate, diethyl N-{(2E)-3-[4-({4-[amino(imino)methyl]phenoxy}carbonyl)phenyl]-2-methyl-2-propenoyl}-L-glutaminate, 4-[amino(imino)methyl]phenyl 4-{(1E)-3-[[benzyl(2-ethoxy-2-oxoethyl)amino]-1-methyl-3-oxo-propenoyl}benzoate, 4-[amino(imono)methyl]phenyl 4-[(1E)-3-(4-benzylpiperazin-1-yl)-2-methyl-3-oxo-1-propenyl]benzoate, 4-[amino(imino)methyl]phenyl 4-[(1E)-3-{[(1R)-2-ethoxy-2-oxo-1-phenylethyl]amino}-2-methyl-3-oxo-1-propenyl)benzoate, 4-[amino(imino)methyl]phenyl 4-{(1E)-3-[(2-ethoxy-2-oxoethyl)(4-fluorophenyl)amino]-2-methyl-3-oxo-1-propenoyl}benzoate, 4-[amino(imino)methyl]phenyl 4-{(1E)-3-[(2-ethoxy-2-oxoethyl)(4-methylphenyl)amino]-2-methyl-3-oxo-1-propenoyl}benzoate, 4-[amino(imino)methyl]phenyl 4-[(4-benzylpiperazin-1-yl)carbonyl]benzoate, 4-[amino(imino)methyl]phenyl 4-[(1E)-3-(4-benzylpiperazin-1-yl)-3-oxo-1-propenyl]benzoate, ethyl N-allyl-N—[(E)-2-methyl-3-[4-(4-amidinophenoxycarbonyl)-phenyl]propenoyl]amino acetate, 4-[amino(imino)methyl]phenyl 4-{(1E)-3-[(2-ethoxy-2-oxoethyl)(2-propynyl)amino]-2-methyl-3-oxo-1-propenyl}benzoate, 4-[amino(imino)methyl]phenyl 4-{(1E)-3-benzyl(2-ethoxy-2-oxoethyl)amino]-3-oxo-1-propenyl}benzoate, diethyl 5-({(2E)-3-[4-({4-[amino(imino)methyl]phenoxy}carbonyl)phenyl]-2-methyl-2-propenoyl}amino)isophthalate, diethyl N-{(2E)-3-[4-({4-[amino(imino)methyl]phenoxy}carbonyl)phenyl]-2-methyl-2-propenoyl}-L-aspartate, ethyl 4-{[{(2E)-3-[4-({4-[amino(imino)methyl]phenoxy}carbonyl)phenyl-2-methyl-2-propenoyl}(2-ethoxy-2-oxoethyl)amino]methyl}benzoate, diethyl 2-({(2E)-3-[4-({4-[amino(imino)methyl]phenoxy}carbonyl)phenyl]-2-methyl-2-propenoyl}amino)malonate, diethyl N-{(2E)-3-[4-({4-[amino(imino)methyl]phenoxy}carbonyl)phenyl]-2-methyl-2-propenoyl}-N-benzyl-L-aspartate, diethyl N-{(2E)-3-[4-({4-[amino(imino)methyl]phenoxy}carbonyl)phenyl]-2-methyl-2-propenoyl}-D-glutaminate, diethyl N-{(2E)-3-[4-({4-[amino(imino)methyl]phenoxy}carbonyl)phenyl]-2-propenoyl}-L-glutaminate, diethyl N-{(2E)-3-[4-({4-[amino(imino)methyl]phenoxy}carbonyl)phenyl]-2-butenoyl}-L-glutaminate, 4-[amino(imino)methyl]phenyl 4-{(1E)-3-[((1R)-2-ethoxy-1-{[(2-ethoxy-2-oxoethyl)sulfanyl]methyl}-2-oxoethyl)amino]-2-methyl-3-oxo-1-propenyl}benzoate, 1-benzyl 5-ethyl N-{(2E)-3-[4-({4-[amino(imino)methyl]phenoxy}carbonyl)phenyl]-2-methyl-2-propenoyl}-L-glutaminate, 5-benzyl 1-ethyl N-{(2E)-3-[4-({4-[amino(imino)methyl]phenoxy}carbonyl)phenyl]-2-methyl-2-propenoyl}-L-glutaminate, 1-benzyl 4-ethylester N-{(2E)-3-[4-({4-[amino(imino)methyl]phenoxy}carbonyl)phenyl]-2-methyl-2-propenoyl}-L-aspartate, 1-benzyl 4-isobutyl N-{(2E)-3-[4-({4-[amino(imino)methyl]phenoxy}carbonyl)phenyl]-2-methyl-2-propenoyl}-L-aspartate, N-{(2E)-3-[4-({4-[amino(imino)methyl]phenoxy}carbonyl)phenyl]-2-methyl-2-propenoyl}-L-aspartate 4-benzyl-1-ethylester, diethyl 2-({(2E)-3-[4-({4-[amino(imino)methyl]phenoxy}carbonyl)phenyl]-2-methyl-2-propenoyl}amino)hexanediate, diethyl 2-({(2E)-3-[4-({4-[amino(imino)methyl]phenoxy}carbonyl)phenyl]-2-methyl-2-propenoyl}amino)heptanedioate, 4-[amino(imino)methyl]phenyl 4-{(1E)-3-[(4-ethoxy-4-oxobutyl)amino]-2-methyl-3-oxo-1-propenyl}benzoate, 4-[amino(imino)methyl]phenyl 4-{(1E)-3-[(2-ethoxy-2-oxoethyl)amino]-2-methyl-3-oxo-1-propenyl}benzoate, diethyl 3-({(2E)-3-[4-({4-[amino(imino)methyl]phenoxy}carbonyl)phenyl]-2-methyl-2-propenoyl}amino)pentanedioate, 4-[amino(imino)methyl]phenyl 4-((1E)-3-{allyl[(2E)-4-ethoxy-4-oxo-2-butenyl]amino}-2-methyl-3-oxo-1-propenyl)benzoate, ethyl N-{(2E)-3-[4-({4-[amino(imino)methyl]phenoxy}carbonyl)phenyl]-2-methyl-2-propenoyl}-4-(ethoxycarbonyl)phenylalaninate, ethyl 4-({[(2R)-2-({(2E)-3-[4-({4-[amino(imino)methyl]phenoxy}carbonyl)phenyl]-2-methyl-2-propenoyl}amino)-3-ethoxy-3-oxopropyl]sulfanyl}methyl)benzoate, ethyl 3-({[(2R)-2-({(2E)-3-[4-({4-[amino(imino)methyl]phenoxy}carbonyl)phenyl]-2-methyl-2-propenoyl}amino)-3-ethoxy-3-oxopropyl]sulfanyl}methyl)benzoate, 4-[amino(imino)methyl]phenyl 4-((1E)-3-{[(1R)-2-ethoxy-1-({[(2E)-4-ethoxy-4-oxo-2-butenyl]sulfanyl}methyl)-2-oxoethyl]amino}-2-methyl-3-oxo-1-propenyl)benzoate, ethyl N-{(2E)-3-[4-({4-[amino(imino)methyl]phenoxy}carbonyl)phenyl]-2-methyl-2-propenoyl}-3-(ethoxycarbonyl)phenylalaninate, ethyl 2-{[(2R)-2-({(2E)-3-[4-((4-[amino(imino)methyl]phenoxy}carbonyl)phenyl]-2-methyl-2-propenoyl}amino)-3-ethoxy-3-oxopropyl]sulfanyl)benzoate, 4-[amino(imino)methyl]phenyl 4-{(1E)-3-[(2-ethoxy-2-oxoethyl)(3-methyl-2-butenyl)amino]-2-methyl-3-oxo-1-propenyl}benzoate, ethyl 2-[(allyl{(2E)-3-[4-({4-[amino(imino)methyl]phenoxy}carbonyl)phenyl]-2-methyl-2-propenoyl}amino)methyl]benzoate, diethyl 2-(allyl{(2E)-3-[4-({4-[amino(imino)methyl]phenoxy}carbonyl)phenyl]-2-methyl-2-propenoyl}amino)malonate, ethyl 3-[(allyl{(2E)-3-[4-({4-[amino(imino)methyl]phenoxy}carbonyl)phenyl]-2-methyl-2-propenoyl}amino)methyl]benzoate, ethyl 4-[(allyl{(2E)-3-[4-({4-[amino(imino)methyl]phenoxy}carbonyl)phenyl]-2-methyl-2-propenoyl}amino)methyl]benzoate, 4-[amino(imino)methyl]phenyl 4-{(1E)-3-[[(2E)-4-ethoxy-4-oxo-2-butenyl](2-ethoxy-2-oxoethyl)amino]-2-methyl-3-oxo-1-propenyl}benzoate, diethyl 2-[(2E)-3-[4-({4-[amino(imino)methyl]phenoxy}carbonyl)phenyl]-2-methyl-2-propenoyl](4-ethoxy-4-oxobutyl)amino]malonate, 4-[amino(imino)methyl]phenyl 4-{(1E)-3-[allyl(4-ethoxy-4-oxobutyl)amino]-2-methyl-3-oxo-1-propenyl}benzoate, 4-[amino(imino)methyl]phenyl 4-{(1E)-3-{(2-ethoxy-2-oxoethyl)[(2E,4E)-hexa-2,4-dienyl]amino}-2-methyl-3-oxo-1-propenyl}benzoate, 4-[amino(imino)methyl]phenyl 4-{(1E)-3-[bis(3-ethoxy-3-oxopropyl)amino]-2-methyl-3-oxo-1-propenyl}benzoate, 4-[amino(imino)methyl]phenyl 4-{(1E)-3-[((1R)-2-ethoxy-1-{[(3-ethoxy-3-oxopropyl)sulfanyl]methyl}-2-oxoethyl)amino]-2-methyl-3-oxo-1-propenyl}benzoate, 4-[amino(imino)methyl]phenyl 4-{(1E)-3-[((1R)-2-ethoxy-1-{[(4-ethoxy-4-oxobutyl)sulfanyl]methyl}-2-oxoethyl)amino]-2-methyl-3-oxo-1-propenyl}benzoate, diethyl N-allyl-N-{(2E)-3-[4-({4-[amino(imino)methyl]phenoxy}carbonyl)phenyl]-2-methyl-2-propenoyl}-L-aspartate, diethyl N-[(2E)-3-(4-{[4-[amino(imino)methyl]-2-methoxycarbonyl)phenoxy}carbonyl}phenyl)-2-methyl-2-propenoyl}-L-glutaminate, methyl 2-[(4-{(1E)-3-[allyl(2-ethoxy-2-oxoethyl)amino]-2-methyl-3-oxo-1-propenyl}benzoyl)oxy]-5-[amino(imino)methyl]benzoate, 4-[amino(imino)methyl]phenyl 4-{(1E)-3-[(2-ethoxy-2-oxoethyl)(isopropyl)amino]-2-methyl-3-oxo-1-propenyl}benzoate, ethyl N-{(2E)-3-[4-({4-[amino(imino)methyl]phenoxy}carbonyl)phenyl]-2-methyl-2-propenoyl}-L-leucinate, diethyl N-{3-[4-({4-[amino(imino)methyl]phenoxy}carbonyl)phenyl]propanoyl}-L-glutaminate, 4-[amino(imino)methyl]phenyl 4-{3-[allyl(2-ethoxy-2-oxoethyl)amino]-3-oxopropyl}benzoate diethyl N-{(2E)-3-[4-({4-[amino(imino)methyl]phenoxy}carbonyl)phenyl]-2-methyl-2-propenoyl}-N-(3-ethoxy-3-oxopropyl)-L-aspartate, 4-[amino(imino)methyl]phenyl 4-{(1E)-3-[(2-ethoxy-2-oxoethyl)(propyl)amino]-2-methyl-3-oxo-1-propenyl}benzoate, 4-[amino(imino)methyl]phenyl 4-{(1E)-3-{[(1S)-1-(ethoxycarbonyl)-2-methylpropyl]amino}-2-methyl-3-oxo-1-propenyl}benzoate, diethyl N-[(2E)-3-(4-{[4-amino(imino)methyl]-2-(ethoxycarbonyl)phenoxy} carbonyl}phenyl)-2-methyl-2-propenoyl]-L-glutaminate, ethyl 2-[(4-{(1E)-3-[allyl(2-ethoxy-2-oxoethyl)amino]-2-methyl-3-oxo-1-propenyl}benzoyl)oxy]-5-[amino(imino) methyl]benzoate, 4-[amino(imino)methyl]phenyl 3-{(1E)-3-[allyl(2-ethoxy—2-oxoethyl)amino]-2-methyl-3-oxo-1-propenyl}benzoate, diethyl N-{(2E)-3-[3-({4-[amino (imino)methyl]phenoxy}carbonyl)phenyl]-2-methyl-2-propenoyl}-L-glutaminate, N-allyl-N-{(2E)-3-[4-({4-[amino(imino)methyl]phenoxy}carbon yl)phenyl]-2-methyl-2-propenoyl}glycine, 4-(allyl{(2E)-3-[4-({4-[amino (imino)methyl]phenoxy}carbonyl)phenyl]-2-methyl-2-propenoyl}amino)butanoic acid, N-{(2E)-3-[4-({4-[amino (imino)methyl]phenoxy}carbonyl)phenyl]-2-methyl-2-propenoyl}-N-[(2E,4E)-hexa-2,4-dienyl]glycine 3-[{(2E)-3-[(4-({4-[amino(imino)methyl]phenoxy}carbonyl)phenyl]-2-methyl-2-propenoyl}(3-ethoxy-3-oxopropyl)amino] propanoic acid, N-{(2E)-3-[4-({4-[amino(imino)methyl] phenoxy}carbonyl)phenyl]-2-methyl-2-propenoyl}-N-(2-carboxyethyl)-β-alanine, N-{(2E)-3-[4-({4-[amino(imino) methyl]phenoxy}carbonyl)phenyl]-2-methyl-2-propenoyl}-L-glutamic acid, (4S)-4-({(2E)-3-[4-({4-[amino(imino) methyl]phenoxy}carbonyl)phenyl]-2-methyl-2-propenoyl}amino)-5-ethoxy-5-oxopentanoic acid, [{(2E)-3-[4-({4-[amino(imino)methyl]phenoxy}carbonyl)phenyl]-2-methyl-2-propenoyl}(3-ethoxy-3-oxopropyl)amino]acetic acid, N-{(2E)-3-[4-({4-[amino(imino)methyl] phenoxy}carbonyl)phenyl]-2-methyl-2-propenoyl}-N-(2-ethoxy-2-oxoethyl)-β-alanine, (2S)-2-({(2E)-3-[4-({4-[amino(imino)methyl]phenoxy}carbonyl)phenyl]-2-methyl-2-propenoyl}amino)-5-ethoxy-5-oxopentanoic acid, 4-[amino(imino)methyl]phenyl 4-{(1E)-3-[(2-ethoxy-2-oxoethyl)(isobutyl)amino]-2-methyl-3-oxo-1-propenyl}benzoate, 4-[amino(imino)methyl]phenyl 4-{(1E)-3-[(2-ethoxy-2-oxoethyl)(isopentyl)amino]-2-methyl-3-oxo-1-propenyl}benzoate, 4-[amino(imino)methyl]phenyl 4-{(1E)-3-[cyclopropyl(2-ethoxy-2-oxoethyl)amino]-2-methyl-3-oxo-1-propenyl}benzoate, 4-[amino(imino)methyl] phenyl 4-{(1E)-3-[allyl(3-ethoxy-3-oxopropyl)amino]-2-methyl-3-oxo-1-propenyl}benzoate, 4-[amino(imino) methyl]phenyl 4-{(1E)-3-[(3-ethoxy-3-oxopropyl)(propyl) amino]-2-methyl-3-oxo-1-propenyl}benzoate, N-{(2E)-3-[4-({4-[amino(imino)methyl]phenoxy}carbonyl)phenyl]-2-methyl-2-propenoyl}-N-isopropylglycine, N-{(2E)-3-[4-({4-[amino(imino)methyl]phenoxy}carbonyl)phenyl]-2-methyl-2-propenoyl}-N-isobutylglycine, N-{(2E)-3-[4-({4-[amino(imino)methyl]phenoxy}carbonyl)phenyl]-2-methyl-2-propenoyl}-N-propylglycine, (4R)-4-({(2E)-3-[4-({4-[amino(imino)methyl]phenoxy}carbonyl)phenyl]-2-methyl-2-propenoyl}amino)-5-ethoxy-5-oxopentanoic acid, 4-[amino(imino)methyl]phenyl 4-{(1E)-3-[(2-ethoxy-2-oxoethyl)(3-ethoxy-3-oxopropyl)amino]-2-methyl-3-oxo-1-propenyl}benzoate, (3S)-3-(allyl{(2E)-3-[4-({4-[amino (imino)methyl]phenoxy}carbonyl)phenyl]-2-methyl-2-propenoyl}amino-4-ethoxy-4-oxobutanoic acid, N-allyl-N-{(2E)-3-[4-({4-[amino(imino)methyl]phenoxy}carbonyl) phenyl]-2-methyl-2-propenoyl}-L-asparagic acid, 4-[amino (imino)methyl]phenyl 4-{(1E)-3-[cyclohexyl(2-ethoxy-2-oxoethyl)amino]-2-methyl-3-oxo-1-propenoyl}benzoate, diethyl 2-[{(2E)-3-[4-({4-[amino(imino)methyl] phenoxy}carbonyl)phenyl]-2-methyl-2-propenoyl}(2-ethoxy-2-oxoethyl)amino]malonate, 4-[amino(imino)methyl]phenyl 4-{(1E)-3-[(3-ethoxy-3-oxopropyl)(isopropyl) amino]-2-methyl-3-oxo-1-propenyl}benzoate, diethyl N-{(2E)-3-[4-({4-[amino(imino)methyl]phenoxy}carbonyl) phenyl]-2-methyl-2-propenoyl}-N-(2-ethoxy-2-oxoethyl)-L-aspartate, diethyl 2-[{(2E)-3-[4-({4-[amino(imino) methyl]phenoxy}carbonyl)phenyl]-2-methyl-2-propenoyl} (3-ethoxy-3-oxopropyl)amino]malonate, [{(2E)-3-[4-({4-[amino(imino)methyl]phenoxy}carbonyl)phenyl]-2-methyl-2-propenoyl}(2-ethoxy-2-oxoethyl)amino]acetic acid, 4-[amino(imino)methyl]phenyl 4-((1E)-3-{allyl[(1S)-2-ethoxy-1-methyl-2-oxoethyl]amino}-2-methyl-3-oxo-1-propenyl}benzoate, diethyl N-allyl-N-{(2E)-3-[4-({4-[amino(imino)methyl]phenoxy}carbonyl)phenyl]-2-methyl-2-propenoyl}-D-aspartate, diethyl N-{(2E)-3-[4-({4-[amino (imino)methyl]phenoxy}carbonyl)phenyl]-2-methyl-2-propenoyl}-N-(2-ethoxy-2-oxoethyl)-D-aspartate, diethyl N—((2E)-3-[4-({4-[amino(imino)methyl] phenoxy}carbonyl)phenyl]-2-methyl-2-propenoyl)-N-(2-ethoxy-2-oxoethyl)-L-aspartate, 4-[amino(imino)methyl] phenyl 4-{(1E)-3-[benzyl(3-ethoxy-3-oxopropyl)amino]-2-methyl-3-oxo-1-propenyl}benzoate, diethyl N-{(2E)-3-[4-({4-[amino(imino)methyl]phenoxy}carbonyl)phenyl]-2-methyl-2-propenoyl}-N-(3-ethoxy-3-oxopropyl)-D-aspartate, 4-[amino(imino) methyl]phenyl 4-{(1E)-3-[[(1R)-2-ethoxy-1-methyl-2-oxoethyl](2-ethoxy-2-oxoethyl) amino]-2-methyl-3-oxo-1-propenyl}benzoate, 4-[amino (imino)methyl]phenyl 4-{(1E)-3-[[(1R)-2-ethoxy-1-methyl-2-oxoethyl](3-ethoxy-3-oxopropyl)amino]-2-methyl-3-oxo-1-propenyl}benzoate, (2S)-2-(allyl{(2E)-3-[4-((4-[amino (imino)methyl]phenoxy}carbonyl)phenyl]-2-methyl-2-propenoyl}amino)-4-ethoxy-4-oxobutanoic acid, diethyl N-{(2E)-3-[4-({4-[amino(imino)methyl]phenoxy}carbonyl) phenyl]-2-methyl-2-propenoyl}-N-(4-ethoxy-4-oxobutyl)-L-aspartate, 2-[((2E)-3-[4-((4-[amino(imino)methyl] phenoxy)carbonyl)phenyl]-2-methyl-2-propenoyl)(4-ethoxy-4-oxobutyl)amino]-3-ethoxy-3-oxopropanoic acid, diethyl N-{(2E)-3-[4-({4-[amino(imino)methyl] phenoxy}carbonyl)phenyl]-2-methyl-2-propenoyl}-N-[(2E)-4-ethoxy-4-oxo-2-butenyl]aspartate, 4-[amino(imino) methyl]phenyl 4-{(1E)-3-[allyl((1R)-2-ethoxy-1-{[(2-ethoxy-2-oxoethyl)sulfanyl]methyl}-2-oxoethyl)amino]-2-methyl-3-oxo-1-propenyl}benzoate, 4-[amino(imino) methyl]phenyl 4-{(1E)-3-[((1R)-2-ethoxy-1-{[(2-ethoxy-2-oxoethyl)sulfanyl]methyl}-2-oxoethyl)(4-ethoxy-4-oxobutyl)amino]-2-methyl-3-oxo-1'-propenyl}benzoate, diethyl 2-[{(2E)-3-[4-({4-[amino(imino)methyl] phenoxy}carbonyl)phenyl]-2-methyl-2-propenoyl}(4-methoxy-4-oxobutyl)amino]malonate, diethyl N-{(2E)-3-[4-({4-[amino(imino)methyl]phenoxy}carbonyl)phenyl]-2-methyl-2-propenoyl}-N-(4-ethoxy-4-oxobutyl)-L-glutamate, diethyl 2-[{(2E)-3-[4-({4-[amino(imino)methyl] phenoxy}carbonyl)phenyl]-2-methyl-2-propenoyl}(isopentyl)amino]malonate, 4-{((2E)-3-[4-({4-[amino(imino)methyl]phenoxy}carbonyl)phenyl]-2-methyl-2-propenoyl)[2-ethoxy-1-(ethoxycarbonyl)-2-oxoethyl]amino}butanoic acid, diethyl 2-[{(2E)-3-[4-({4-[amino(imino)methyl] phenoxy}carbonyl)phenyl]-2-methyl-2-propenoyl}(6-ethoxy-6-oxohexyl)amino]malonate, ethyl N—((2E)-3-[4-({4-[amino(imino)methyl]phenoxy}carbonyl)phenyl]-2-methyl-2-propenoyl)-N-(4-ethoxy-4-oxobutyl)-L-phenylalaninate, diethyl N-allyl-N-{(2E)-3-[4-({4-[amino (imino)methyl]phenoxy}carbonyl)phenyl]-2-methyl-2-propenoyl}-L-glutamate, ethyl N-{(2E)-3-[4-({4-[amino (imino)methyl]phenoxy}carbonyl)phenyl]-2-methyl-2-propenoyl}-N-(4-ethoxy-4-oxobutyl)-L-leucinate, diethyl 3-[{(2E)-3-[4-({4-[amino(imino)methyl] phenoxy}carbonyl)phenyl]-2-methyl-2-propenoyl}(isopentyl)amino]pentanedioate, diethyl 3-[{(2E)-3-[4-({4-[amino (imino)methyl]phenoxy}carbonyl)phenyl]-2-methyl-2-propenoyl}(propyl)amino]pentanedioate, diethyl 3-[{(2E)-3-[4-({4-[amino(imino)methyl]phenoxy}carbonyl)phenyl]-2-methyl-2-propenoyl}(cyclohexyl)amino]pentanedioate, 4-[amino(imino)methyl]phenyl 4-{(1E)-3-[(2-ethoxy-2- oxoethyl)(hexyl)amino]-2-methyl-3-oxo-1-propenyl}benzoate, 4-[amino(imino)methyl]phenyl 4-{(1E)-3-[(2-ethoxy-2-oxoethyl)(1-propylbutyl)amino]-2-methyl-3-oxo-1-propenyl}benzoate, N-{(2E)-3-[4-({4-[amino(imino)methyl]phenoxy}carbonyl)phenyl]-2-methyl-2-propenoyl)-N-hexylglycine, N—((2E)-3-[4-((4-[amino(imino)methyl]phenoxy}carbonyl)phenyl]-2-methyl-2-propenoyl)-N-isopentylglycine, 4-[amino(imino)methyl]phenyl 4-((1E)-3-[(2-ethoxy-2-oxoethyl)/(methyl)amino]-2-methyl-3-oxo-1-propenyl)benzoate, N-{(2E)-3-[4-({4-[amino(imino)methyl]phenoxy}carbonyl)phenyl]-2-methyl-2-propenoyl}-N-cyclohexylglycine, N-{(2E)-3-[4-({4-[amino(imino)methyl]phenoxy}carbonyl)phenyl]-2-methyl-2-propenoyl}-N-cyclopropylglycine, 4-[amino(imino)methyl]phenyl 4-{(1E)-3-[cyclopentyl(2-ethoxy-2-oxoethyl)amino]-2-methyl-3-oxo-1-propenyl}benzoate, 4-[amino(imino)methyl]phenyl 4-{(1E)-3-[cyclobutyl(2-ethoxy-2-oxoethyl)amino]-2-methyl-3-oxo-1-propenyl}benzoate, N—((2E)-3-[4-({4-[amino(imino)methyl]phenoxy)carbonyl)phenyl]-2-methyl-2-propenoyl}-N-cyclopentylglycine, 4-[amino(imino)methyl]phenyl 4-{(1E)-3-[butyl(2-ethoxy-2-oxoethyl)amino]-2-methyl-3-oxo-1-propenyl}benzoate, N-{(2E)-3-[4-({4-[amino(imino)methyl]phenoxy}carbonyl)phenyl]-2-methyl-2-propenoyl}-N-butylglycine, 4-[amino(imino)methyl]phenyl 4-{(1E)-3-[(3-ethoxy-3-oxopropyl)(methyl)amino]-2-methyl-3-oxo-1-propenyl}benzoate, 4-[amino(imino)methyl]phenyl 4-((1E)-3-[(3-ethoxy-3-oxopropyl)(ethyl)amino]-2-methyl-3-oxo-1-propenyl) benzoate, N-{(2E)-3-[4-({4-[amino(imino)methyl]phenoxy}carbonyl)phenyl]-2-methyl-2-propenoyl}-N-propyl-β-alanine, N-{(2E)-3-[4-({4-[amino(imino)methylphenoxy}carbonyl)phenyl]-2-methyl-2-propenoyl}-N-isopropyl-β-alanine, 4-[amino(imino)methyl]phenyl 4-{(1E)-3-[(2-ethoxy-2-oxoethyl)(ethyl)amino]-2-methyl-3-oxo-1-propenoyl}benzoate, N-{(2E)-3-[4-({4-[amino(imino)methyl]phenoxy}carbonyl)phenyl]-2-methyl-2-propenoyl}-N-ethylglycine, N-{(2E)-3-[4-({4-[amino(imino)methyl]phenoxy}carbonyl)phenyl]-2-methyl-2-propenoyl}-N-(1-propylbutyl)glycine, N-{(2E)-3-[4-({4-[amino(imino)methyl]phenoxy}carbonyl)phenyl]-2-methyl-2-propenoyl}-N-methylglycine, N-{(2E)-3-[4-({4-[amino(imino)methyl]phenoxy}carbonyl)phenyl]-2-methyl-2-propenoyl}-N-methyl-β-alanine, N-{(2E)-3-[4-({4-[amino(imino)methyl]phenoxy}carbonyl)phenyl]-2-methyl-2-propenoyl}-N-ethyl-β-alanine, and N-allyl-N-{(2E)-3-[4-({4-[amino(imino)methyl]phenoxy}carbonyl)phenyl]-2-methyl-2-propenoyl}-β-alanine, their salts and solvates, and prodrugs thereof.

The compound represented by the general formula (I) preferably may be exemplified by the compounds represented by the formula (I-1):

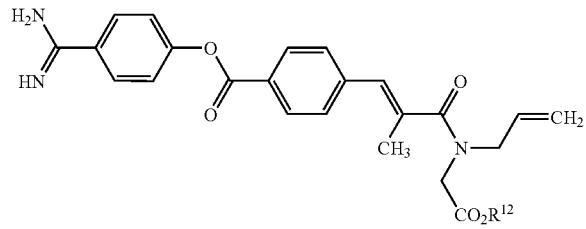

(I-1)

(wherein $R^{12}$ is a hydrogen atom or a C1-4 alkyl group), more preferably the compound of the formula (I-1) wherein $R^{12}$ is ethyl is N-allyl-N—[(E)-2-methyl-3-[4-(4-amidinophenoxycarbonyl)-phenyl]propenoyl]amino acetate, that is, the compound represented by the formula (I-1a):

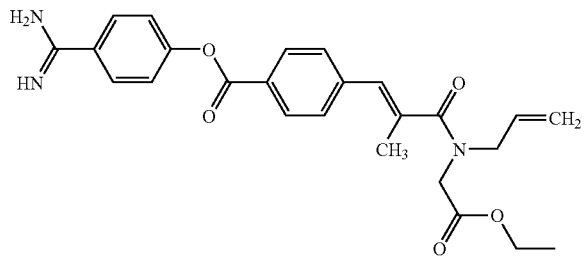

(I-1a)

and the compound of the formula (I-1) wherein $R^{12}$ is a hydrogen atom is N-allyl-N-{(2E)-3-[4-({4-[amino(imino)methyl]phenoxy}carbonyl)phenyl]-2-methyl-2-propenoyl}glycine, that is, the compound represented by the formula (I-1b):

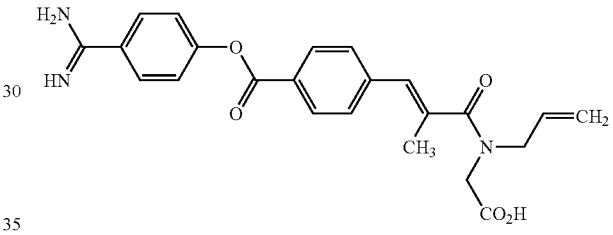

(I-1b)

its salts and solvates, and prodrugs thereof. Said compounds are found to exhibit protease inhibitory activities against trypsin, thrombin, pancreatic and plasma kallikrein, plasmin and the like, as well as leukotriene B4 (LTB4) receptor antagonistic action (see JP-A H8-143529).

In the specification, the term "GLP-1" means glucagon like peptide-1.

In the specification, the expression "GLP-1 elevation promotion or generation enhancement" means the action that may involve the GLP-1 generation and/or inductive secretion.

In the specification, the expression "GLP-1 generation and/or inductive secretion" means the action which is selected from the induction caused by increases of GLP-1 mRNA expression, the induction caused by increases of GLP-1 protein synthesis, the induction caused by increases of secretion from the GLP-1 producing cell, the induction caused by increases of GLP-1 secretion into blood and inhibition or suppression of degradation of GLP-1 mRNA and/or GLP-1 in each of such processes.

In the specification, the expression "suppression of GLP-1 reduction" means the action that may involve the inhibitory or suppressory action of GLP-1 degradation.

In the specification, the expression "blood-sugar elevation suppression and/or blood-sugar reduction" means that such an effect may be exerted as can permit the compound in question to exhibit one or more kinds of the activities selected from the activity(ies) of suppressing the elevation of the fasting and nonfasting blood-sugar levels and/or lowering the said blood sugar levels, the activity(ies) of suppressing the elevation of the blood-sugar level up to two hours after sugar loading and/or lowering the blood sugar levels, and the activity(ies) of suppressing the elevation of $HbA_{1C}$ and/or lowering $HbA_{1C}$. Furthermore, the expression preferably means that such an effect may be exerted as may permit the compound in question to exhibit one or more kinds of the activities selected from the activities of suppressing the fasting blood-sugar levels to below about 126 mg/dL and suppressing the blood sugar level up to two hours after sugar loading to below about 200 mg/dL, and the activity of suppressing $HbA_{1C}$ to below about 6.1%, and especially means that such an effect may be exerted as may permit the compound in question to exhibit one or more kinds of the activities selected from the activities of suppressing the fasting blood-sugar levels to below about 110 mg/dL and suppressing the blood sugar level up to two hours after sugar loading to below about 140 mg/dL, and the activity of suppressing $HbA_{1C}$ to below about 5.5%.

In the specification, the term "glucagon-amount suppression" means the activities which may include the activity of lowering the fasting blood-glucagon level down to below about 430 pg/mL.

In the specification, the term "insulin-synthesis promotion" means the action which may include the action of increasing the insulinogenic index up to more than about 0.4, preferably more than about 0.8.

In the specification, the term "blood-lipid amelioration or lipid reduction" means the such an action may be displayed as may permit the compound in question to accomplish one or more kinds selected from the reduction of the fasting total cholesterol level, elevation of the HDL (High Density Lipoprotein) cholesterol level, reduction of the LDL (Low Density Lipoprotein) cholesterol level, reduction of the free fatty acid level and reduction of the neutral fat (triglyceride, etc.) level.

The expression "reduction of the total cholesterol level" means that the activity of reducing the total cholesterol level may be exhibited, and preferably means the total cholesterol level of below about 240 mg/dL at fasting, particularly preferably below about 220 mg/dL at fasting.

The expression "elevation of the HDL cholesterol level" means that the activity of elevating the HDL cholesterol level may be exhibited, and means the activity of increasing the HDL cholesterol level to preferably not less than about 40 mg/dL at fasting, particularly preferably not less than about 50 mg/dL at fasting.

The expression "reduction of the LDL cholesterol" means that the action of reducing the LDL cholesterol level may be exhibited, and preferably means the action of reducing the LDL cholesterol level to below about 150 mg/dL at fasting.

The expression "reduction of the free fatty acid" means that the activity of reducing the free fatty acid level may be exhibited, and preferably means the action of reducing the free fatty acid level to below about 620 µEq/L.

The expression "reduction of the neutral fat level" means that the activity of reducing the neutral fat level may be exhibited, and preferably means the action of reducing the neutral fat level to below about 200 mg/dL at fasting, more preferably below about 150 mg/dL at fasting.

In the specification, the expression "promotion of the pancreatic beta-cell regeneration" means the promotion each of the proliferation of the pancreatic beta cells which decreased in vivo, the differentiation of the stem cells (e.g., the embryonic-stem cells, etc.) to the insulin-secreting cells and/or the proliferation of the stem cells or the somatic stem cells (e.g., the pancreatic stem epithelial cells etc.) to the insulin-secreting cells and/or the proliferation of the somatic stem cells, and additionally includes the hyperfunction through hypertrophy of the pancreatic beta cells.

Unless otherwise specified, all the isomers are included in the present invention. For example, the alkyl, alkenyl, alkynyl, alkoxy, alkylthio, alkylene, alkenylene and alkynylene groups are understood to include their straight-chain or branched ones. In addition, isomers in relation to the double bond, ring, fused ring (E-, Z-, cis-, trans-isomers), isomers generated due to existence of the asymmetric carbon atom(s) (R- and S-isomers, α- and β-configurations, enantiomer, diastereomer), optically active isomers (D-, L-, d-, l-isomers), polar compounds generated by chromatographic separation (high-polar compound, less-polar compound), equilibrium compounds, rotational isomers, mixtures thereof at arbitrary ratios and racemic mixtures are also included in the present invention.

In the present invention, unless otherwise indicated and as is apparent for those skilled in the art, the symbol ⋯ indicates that it is bound to the opposite side of the sheet of paper (namely α-configuration), the symbol ╱ indicates that it is bound to the front side of the sheet of paper (namely β-configuration), the symbol ⌇ indicates that it is a α-configuration, β-configuration or a mixture thereof which may be mixed at arbitrary ratios and the symbol ╱ indicates that it is a mixture of α-configuration and β-configuration.

The compounds represented by the general formula (I) can be converted to salts thereof by the known methods. As the salts, there may be mentioned salts with alkali metals, salts with alkaline earth metals, ammonium salts, amine salts, acid addition salts and the like. Such salts preferably are pharmaceutical acceptable salts. Particularly preferably, they are acid addition salts.

Water soluble salts are preferred. The suitable salts may be exemplified by salts with alkali metals (e.g., potassium, sodium, etc.), salts with alkaline earth metals (e.g., calcium, magnesium, etc.), ammonium salts, salts with pharmaceutical acceptable organic amines (e.g., triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.).

Acid addition salts are preferably water-soluble. The suitable acid addition salts may be exemplified by salts with inorganic acids (e.g., hydrochloride, dihydrochloride, hydrobromide, hydroiodide, sulfate, phosphate, nitrate etc.), and salts with organic acids (e.g., acetate, trifluoroacetate, lactate, tartrate, oxalate, fumarate, maleate, benzoate, citrate, methanesulfonate, dimethanesulfonate, ethanesulfonate, benzenesulfonate, toluenesulfonate, isethionate, glucuronate, gluconates, etc. Preferably, hydrochloride, dihydrochloride, dimethanesulfonate and methanesulfonate are mentioned.

The compound represented by the general formula (I), a salt thereof, can be also converted into a solvate. The solvate preferably includes non-toxic and water-soluble ones. A suitable solvate of the present invention includes the solvates with solvents, such as water, alcohol-based solvents (e.g., ethanol, etc.), etc.

The prodrug of the compounds represented by the general formula (I) means, a compound is converted to the compound represented by the general formula (I) through the reaction with enzymes, gastric acids and so on within the living body.

The prodrug of the compound represented by the general formula (I) include, when the compound represented by the general formula (I) has an amino group, the compound the amino group of which is acylated, alkylated, or phosphorylated (e.g., the compound represented by the general formula (I) where the amino is eicosanoated, alanylated, pentylaminocarbonylated, (5-methyl-2-oxo-1,3-dioxolan-4-yl)methoxycarbonylated, tetrahydrofuranated, pyrrolidylmethylated, pivaloyloxymethylated, acetoxymethylated or tert-butylated, and the like); when the compound represented by the general formula (I) has a hydroxy group, the prodrug is the compound the hydroxy of which is acylated, alkylated, phosphorylated or borated (e.g., the compound represented by the general formula (I) where the hydroxy group is acetylated, palmitoylated, propanoylated, pivaloylated, succinylated, fumarylated, alanylated or dimethylaminomethylcarbonylated, and the like); when the compound represented by the general formula (I) has a carboxy group, the prodrug is the compound the carboxyl of which is esterified or amidated (e.g., the compound represented by the general formula (I) where the carboxyl group is ethylesterified, phenylesterified, carboxymethylesterified, dimethylaminomethylesterified, pivaloyloxymethylesterified, ethoxycarbonyloxyethylesterified, phthalidylesterified, (5-methyl-2-oxo-1,3-dioxolen-4-yl)methylesterified, cyclohexyloxycarbonylethylesterified or methylamidated, and the like); when the compound represented by the general formula (I) has a carboxy group, the prodrug is the compound the carboxyl of which is substituted with a hydroxymethyl group and the like. These compounds can be prepared by the method known per se. In addition, the prodrug of the compound represented by the general formula (I) may be either of solvate and non-solvate.

[Processes for Producing the Compound According to the Present Invention]

In the specification, the protease-inhibiting compound can be prepared in accordance with the methods described in JP-A S52-89640, JP-A H08-109164, JP-A H07-206801, JP-A H08-143529 or JP-A S61-33173, or methods similar thereto. Particularly, the compound according to the present invention as represented by the general formula (I) can be prepared by the methods described in JP-A H08-109164, or methods similar thereto.

[Application to Pharmaceutical Preparations]

The compound of the present invention is considered to be useful as a preventive and/or therapeutic agent for diabetes, such as non-insulin-dependent diabetes mellitus, ketosis-resistant diabetes, maturity onset diabetes of youth, insulin-dependent diabetes mellitus, ketosis prone diabetes, juvenile diabetes, insulinopenic diabetes, starvation diabetes, latent diabetes (potential diabetes), unstable diabetes, subclinical diabetes, pancreatic diabetes, or prediabetic state (borderline diabetes) and the like.

Consequently, the compound of the present invention is considered to be useful as a preventive and/or therapeutic agent for complications of diabetes, one or more kinds selected from the complications, such as diabetic acidosis, diabetic neuropathy, diabetic polyneuropathy, diabetic myelopathy, necrobiosis lipoidica diabeticorum, diabetic gastroparesis, diabetic xanthoma, diabetic gangrene, diabetic arthropathy, diabetic balanitis, diabetic thoracic radiculopathy, diabetic amyotrophy, diabetic coma, diabetic glomerulosclerosis, diabetic lipemia, diabetic gingivitis, diabetic eczema, diabetic neuropathic cachexia, diabetic tabetic neurosyphilis, diabetic breathing, rubeosis iridis diabetic, diabetic cataract, diabetic dermopathy, diabetic nephropathy and diabetic retinopathy, and the like, as well as macroangiopathies, such as arterial sclerosis, ischemic heart disease, cardiac infarction, angina, cerebrovascular disorders, apoplexy, stroke, arteriosclerosis obliterans and intermittent claudication and the like.

The compound of the present invention, which exhibits the LTB4 (leukotrieneB4) antagonistic effect (JP-A H08-143529) in addition to the ameliorating effects of blood sugar and lipid, etc., is considered to be useful for prevention and/or therapy of arterial sclerosis which is included in the complications of diabetes (see Arterioscler Thromb. Vasc. Biol., 24, 369-375 (2004)). The deadly quartet (diabetes, hyperlipidemia, hypertension and obesity (accumulation of visceral fat)) or syndrome X (abnormal glucose tolerance, insulin resistance, high VLDL, low HDL and hypertension) and the like, which were once referred to collectively as a multiple risk factor syndrome, are recently called the metabolic syndrome, attracting increased attention as a cause for the development of cardiovascular diseases owing to arterial sclerosis (e.g., cardiac infarction, angina, stroke, arteriosclerosis obliterans and the like).

Additionally, the compound of the present invention is considered to be useful as a preventive and/or therapeutic agent for the diseases being preventable and/or treatable diseases with GLP-1. The disease being preventable and/or treatable disease with GLP-1 is understood to denote the diseases which are preventable and/or treatable through elevation, maintenance and/or suppressed reduction of the blood and/or tissue GLP-1 levels. Examples of such diseases include the above-described diseases, as well as glucagonoma or glucagonoma syndrome and hyperglucagonemia, etc.

[Toxicity]

The compound of the present invention shows extremely low toxicity, and is adequately safe enough to use as a medicinal drug.

The compound of the present invention, its salt and solvate, or a prodrug thereof may be administered to a patient in combination with other pharmaceutical preparations or as a concomitant preparation to accomplish the following purposes:

1) To complement and/or enhance the prevention and/or treatment effect of the above-described diseases produced by the compound of the present invention;
2) To improve the pharmacokinetics/absorption of the compound of the present invention and reduce the dose of the compound of the present invention; and/or
3) To eliminate the side effects of the compound of the present invention.

The concomitant preparation comprising the compound of the present invention and other medicinal drugs may be administered to a patient in the form of a combination agent or preparation having these components incorporated in one pharmaceutical preparation or may take the form of making administration in separate pharmaceutical preparations. In the case of administration as processed in separate pharmaceutical preparations, such administration includes simultaneous and time-difference administrations. In the case of time-difference administration, the medicinal drug of the present invention may be administered to a patient in advance, followed by application of other medicinal drugs, or alternatively, other medicinal drugs may be administered to a patient in advance, followed by application of the compound of the present invention, whereby the individual methods of the administration may be the same or different.

The above-described other medicinal drugs may be low-molecular compounds and may be high-molecular proteins, polypeptides, polynucleotides (DNA, RNA, and gene), anti-senses, decoys, antibodies or vaccines and so on. The dose of the other medicinal drugs can be appropriately selected on the basis of their clinical doses taken as a standard. In the meanwhile, the formulation ratio of the compound of the present invention to the other medicinal drugs can be appropriately selected on the basis of the age and weight of a subject, method and time of administration, type and symptom of the disease to be treated, combination, etc. For example, 0.01 to 100 parts by weight of the other medicinal drug may be used against 1 part by weight of the compound of the present invention. Not less than arbitrary two kinds of the other medicinal drugs may be administered to a patient in combinations at appropriate ratios. The other medicinal drugs to complement and/or enhance the prevention and/or treatment effect(s) of the compound of the present invention do not only include ones which have been found out so far in the past but also will be discovered from now onward in the future on the basis of the above-mentioned mechanism.

The other medicinal drugs may be exemplified by aldose reductase inhibitor, insulin preparation, insulin secretagogue, fast insulin secretagogue, sulfonylurea drug, biguanides, GLP-1 analogue, DPP-IV inhibitor, a-glycosylase inhibitor, glucagon antagonist, PPAR agonist, PPAR-γ agonist, PPAR-a agonist, PPAR-a and γ agonists, fructose-bisphosphatase inhibitor, GSK-3β inhibitor, low affinity sodium/glucose cotransporter inhibitor, Glut4 transport promoter, phosphatidyl inositol stimulator, phosphatase inhibitor, prostaglandin synthesis stimulator, trypsin phosphatase inhibitor, hydroxysteroid dehydrogenase inhibitor, carnitine palmitoyltransferase inhibitor, lipase inhibitor, lipid peroxidative inhibitor, dopamine D2 agonist, β3 agonist, amylin agonist, histamine $H_1$ antagonist, sodium channel antagonist, adenosine A2 agonist, potassium channel opener, antioxidant drug, 5-HT uptake inhibitor, 5-HT2C agonist, TNF-a antagonist, anti CD3 monoclonal antibody, anti GDF-8 antibody, IL-2 agonist, recombinant human IGF-1, somatostatin agonist, PKC inhibitor, NGF agonist, EGF agonist, PDGF agonist, immunosuppressive drug, the other remedies for diabetes and remedy for complications of diabetes.

The aldose reductase inhibitor may be exemplified by risarestat, imirestat, sorbinil, fidarestat, zenarestat, ponalrestat, tolrestat, zopolrestat, epalrestat, metosorbinil, minalrestat, lindolrestat, JTT-811, SG-210, bimoclomol, AL-1567, TAT, AS-3201, NZ-314, AD-5467 and the like.

The insulin preparation may be exemplified by insulin detemir, insulin aspart, insulin glargine, insulin glulysine, insulin lyspro, insulin (recombinant) (tradename; Isuhuman), insulin inhalation, transdermal insulin, insulin semi-synthetic, insulinoral, HMR-4006, N,N-344, INGAP peptide, albulin, basulin, AI-401 and the like.

The insulin secretagogue means, for example, repaglinide, miglitol, exenatide, AVE-0010 and the like.

Fast insulin secretagogue may be exemplified by nateglinide, mitiglinide calcium hydrate and the like.

The sulfonylurea drug may be exemplified by tolbutamide, glyclopyramide, acetohexamide, chlorpropamide, tolazamide, gliclazide, glibenclamide, glimepiride and the like.

The biguanides may be exemplified by metformin, buformin and the like.

The GLP-1 analogue may be exemplified by insulinotropin, liraglutide, CJC-1131, GLP-1, R-1583, LY-307161, rGLP-1 (Betatropin) and the like.

The DPP-IV inhibitor may be exemplified by LAF-237, P-32/98, P-93/01, TS-021, 815541, 825964, 823093, TA-6666, MK-0431 and the like.

The a-glycosylase inhibitor may be exemplified by miglitol, voglibose, acarbose and the like.

The glucagon antagonist may be exemplified by N,N-2501 and the like.

The PPAR agonist may be the agonists for PPAR a, γ and d receptors and may also be any combinations of not less than two thereof, being exemplified by GW-677954, GW-544, bexaroten and the like.

The PPAR-γ agonist may be exemplified by pioglitazone hydrochloride, rosiglitazone maleate, balaglitazone, R-483, netoglitazone, naveglitazar, T-131, SUN-E7001, CLX-0921 and the like.

The PPAR-a agonist may be exemplified by K-111, LY-510929, AVE-0847, AVE-8134 and the like.

The PPAR-a and γ agonists may be exemplified by muraglitazar, tesaglitazar, TAK-559, GW-409544, ONO-5129 and the like.

The fructose•bisphosphatase inhibitor may be exemplified by CS-917, MB06322 and the like.

The SK-38 inhibitor may be exemplified by CT118637, GI179186X, CP-70949, GW784752X, GW784775X and the like.

The low-affinity sodium/glucose cotransporter inhibitor may be exemplified by T-1095, KGT-1251, AVE-2268 and the like.

The glut-4 transport promoter may be exemplified by YM-1919 and the like.

The phosphatidyl inositol stimulator may be exemplified by reglitazar and the like.

The insulin sensitivity enhancer may be exemplified by FK-614, MBX-102, CLX-0901, dexlipotam, GPI-5693 and the like.

The phosphatase inhibitor may be exemplified by ingliforib, AVE-5688 and the like.

The prostaglandin synthesis stimulator may be exemplified by tarabetic and the like.

The trypsin phosphatase inhibitor may be exemplified by ISIS-113715 and the like.

The hydroxysteroid dehydrogenase inhibitor may be exemplified by BVT-3498, AMG-331 and the like.

The carnitine palmitoyltransferase inhibitor may be exemplified by ST-1326 and the like.

The lipase inhibitor may be exemplified by orlistat, ATL-962 and the like.

The lipid peroxidative inhibitor may be exemplified by tirilazad mesilate and the like.

The dopamine D2 agonist may be exemplified by bromocriptine mesilate, uridine and the like.

The β3 agonist may be exemplified by YM-178, solabegron hydrochloride, N-5984, LY-377601 and the like.

The amylin agonist may be exemplified by pramlintide acetate and the like.

The histamine $H_1$ antagonist may be exemplified by ReN-1869 and the like.

The sodium channel antagonist may be exemplified by oxcarbazepine and the like.

The adenosine A2 agonist may be exemplified by MRE-0094 and the like.

The potassium channel opener may be exemplified by NN-141 and the like.

The antioxidant drug may be exemplified by EGb-1869 and the like.

The 5-HT uptake inhibitor may be exemplified by duloxetine hydrochloride and the like.

The 5-HT2C agonist may be exemplified by APD-356 and the like. The TNF-a antagonist may be exemplified by BLX-1002 and the like.

The anti-CD3 monoclonal antibody may be exemplified by TRX-4 and the like.

The anti-GDF-8 antibody may be exemplified by MYO-029 and the like.

The IL-2 agonist may be exemplified by denileukin diftitox and the like.

The recombinant human IGF-1 may be exemplified by mecasermin renfabate, somatomedin-I (recombinant), mecasermin (recombinant), PV-705, pegvisomant and the like.

The somatostatin agonist may be exemplified by BIM-23190 and the like.

The RKC inhibitor may be exemplified by ruboxistaurin and the like.

The NGF agonist may be exemplified by TAK-428 and the like.

The EGF agonist may be exemplified by DWP-401 and the like.

The PDGF agonist may be exemplified by becaplermin and the like.

The immunosuppressant may be exemplified by tiplimotide, AVE-0277, NBI-6024, rhGAD65 and the like.

The other drugs for diabetes or complications of diabetes may be exemplified by pyridoxamine hydrochloride, pyrazinoylguanidine, capsaicin, S-15261, CS-011, R-1439, R-765, R-1438, R-1440, AnervaX. RA, V-411, Gluconoct, TAK-654, c-3347, CKD-401, ESP-A, Y-128, QR-333, EXO-226, P-57, second-generation leptin, RO-63-8695, DI-5012 and the like. Further, the other medicinal drugs may be exemplified by antihypertensive drug, diuretic drug, remedy for hyperlipidemia, improvement drug for circulation, remedy for apoplexy, remedy for renal disease, remedy for pancreatic disease, antiplatelet drug, antiatherogenic drug, anti inflammatory drug and the like.

The antihypertensive drug may be exemplified by calcium antagonist, angiotensin II synthetase inhibitor, angiotensin II antagonist and the like. It means, for example, enalapril maleate, doxazosin mesylate, imidapril hydrochloride, temocapril hydrochloride, nilvadipine, manidipine hydrochloride, lisinopril, betaxolol hydrochloride, cilnidipine, celiprololhydrochloride, nipradilol, alacepril, cilazapril, metoprolol tartrate, barnidipine hydrochloride, trandolapril, quinapril hydrochloride, benazepril hydrochloride, efonidipine hydrochloride, bunazosin hydrochloride, captopril, delaprilhydrochloride, telmisartan, bopindolol malonate, urapidil, felodipine, terazosin hydrochloride, amosulalol hydrochloride, aranidipine, cadralazine, tilisolol hydrochloride, candesartan, losartan potassium, valsartan, atenolol, hydrochlorothiazide, methyldopa, nifedipine, nitroprusside sodium and the like.

The diuretic drug may be exemplified by torasemide, amiloride, furosemide, hydrochlorothiazide, mannitol, isosorbide, azosemide, spironolactone and the like.

The remedy for hyperlipidemia may be exemplified by PPAR a and d agonist, HMG-CoA reductase inhibitor, cholesterol absorption inhibitor and the like, being specifically exemplified by aluminum clofibrate, atorvastatin calcium hydrate, bezafibrate, clinofibrate, clofibrate, fenofibrate, cholestimide, cholestyramine, sodium dextran sulfate, elastase, fluvastatin sodium, niceritrol, nicomol, pitavastatin calcium, polyenephosphatidylcholine, pravastatin sodium, probucol, simvastatin, soysterol, alprostadil, nicergoline, nicardipine hydrochloride, tocopherol nicotinate, ifenprodil tartrate, argatroban, epoprostenol sodium, polystyrene sodium, amezinium mesylate, citicoline, fasudil hydrochloride hydrate, lomerizine hydrochloride, nizofenone fumarate and the like.

The improvement drug for circulation may be exemplified by vasodepressor, platelet aggregation inhibitor, thrombolytic drug and the like, being specifically exemplified by butoctamide semisuccinate, fosphenyloin disodium, ozagrel sodium, amantadine hydrochloride, idebenone, nicergoline, arotinolol hydrochloride, benidipine hydrochloride, carvedilol, perindopril erbumine, losartan potassium, candesartan cilexetil, bosentan, irbesartan, fasudil hydrochloride hydrate, nicorandil, pravastatin sodium, eptifibatide, ethyl icosapentate, cilostazol, clopidogrel sulfate, abciximab, ximelagatran, alteplase, tisokinase, rosiglitazone maleate and the like.

The remedy for apoplexy may be exemplified by ozagrel sodium, argatroban, edaravone, aspirin, ticlopidine, cilostazol, warfarin and the like.

The remedy for renal disease is specifically exemplified by dilazep hydrochloride, dipyridamole, icodextrin, persantin, comelian, predonine, solmedrol, endoxane, imulan, bredinin, sandimmune, heparin, warfarin, renivace, captoril and the like. The remedy for pancreatic disease may be exemplified by ulinastatin, gabexate mesilate, camostat mesilate, nafamostat mesilate and the like.

The antiplatelet drug may be exemplified by dalteparin sodium, danaparoid sodium, heparin calcium, heparin sodium, heparin-like substance, parnaparin sodium, reviparin sodium, sodium citrate, warfarin potassium and the like.

The antiatherogenic drug may be exemplified by pravastatin, simvastatin, clofibrate, clinofibrate, bezafibrate, cholestyramine, probucol, niceritrol, eicosapentaenoic acid, ticlopidine, cilostazol, beraprost, limaprost and the like.

The anti-inflammatory drug may be exemplified by NSAID (nonsteroidal anti inflammatory drug), selective COX (cyclooxygeanase) II inhibitor and the like, being specifically exemplified by aspirin, loxonin, diclofenac, celecoxib, tiaprofenic acid, alminoprofen, flurbiprofenaxetil, zaltoprofen, suprofen, ketoprofen, pranoprofen, fentiazac, droxicam, ibuprofen, aceclofenac, amfenac sodium, tenoxicam, oxaprozin, piroxicam, emorfazone, tolfenamic acid, indometacin farnesil, proglumetacin maleate, sulindac, mofezolac, etodolac, lonazolac calcium, ampiroxicam, mesalazine, deflazacort, nimesulid, etoricoxib, ketorolac trometamol, parecoxib, lobenzarit disodium, auranofin, loxoprofen sodium, bucillamine, actarit, piroxicam cinnamate, nabumetone, salazosulfapyridine, lornoxicam, meloxicam, prednisolone farnesylate, diacerein, rofecoxib, valdecoxib, dexamethasone palmitate, fluticasone propionate, methylprednisolone suleptanate, budesonide, difluprednate, dexamethasone propionate, diflorasone diacetate, prednisolone valerate-acetate, hydrocortisone butyrate propionate, clobetasone butyrate, deprodone propionate, halobetasol propionate, halcinonide, amcinonide, betamethasone butyrate propionate, mometasone furoate, etofenamate, tacalcitol, ketoprofen, flurbiprofen, ufenamate, felbinac, beclometasone dipropionate, azulene sodium sulfonate, orgotein, mizoribine, methotrexate and the like.

The mass ratio of the compound according to the present invention to the other medicinal drug is not particularly limited.

The other medicinal drugs may be administered to a patient in combinations of not less than arbitrary two thereof.

In using the compounds according to the present invention or the concomitant preparation comprising the compound according to the present invention and the other medicinal drugs for the above-described purpose, such compounds are normally administered to a patient systemically or topically, and orally or parenterally.

The dose of the compounds according to the present invention varies depending on the patient's age, body weight, symptom, therapeutic effect, method of administration method, length of time of treatment and so on, and such compounds are usually administered to an adult patient orally once or several times per day each at a dose in the range from 1 μg to 1 g, or parentally once or several times per day each at a does in the range from 0.1 μg to 300 mg or through sustained intravenous infusion over the period in the range of 1 hour to 24 hours per day.

As described above, naturally, the dose varies depending upon a variety of conditions, and the doses of less than the above-mentioned ones may in some instances suffice or the doses in excess of the above-mentioned ones may in some cases be needed.

In administering to a patient the compound of the present invention or the concomitant preparation comprising the compound of the present invention and other medicinal drugs, they are used in the form of a solid or liquid preparation for internal use for oral administration, a sustained-release preparation for oral administration, or an injectable solution, preparation for external application, inhalant or suppository for parenteral administration, and the like.

Examples of the solid preparation for internal use for oral administration include tablet, pill, capsule, powder and granule preparations, etc. Examples of the capsule preparation include hard and soft capsules.

In such solid preparation for internal use, one or more active substances are used as such or after being admixed with a vehicle (e.g., lactose, mannitol, glucose, microcrystalline cellulose, starch, etc.), binder (e.g., hydroxypropylcellulose, polyvinyl pyrrolidone, magnesium metasilicoaluminate, etc.), disintegrant (e.g., calcium fibrinoglycolate, etc.), lubricant (e.g., magnesium stearate, etc.), stabilizer, dissolution aid (e.g., glutamic acid, aspartic acid, etc.) and the like and processing the mixture into a pharmaceutical preparation in accordance with the ordinary method. There may be provided coating with a coating agent (e.g., white sugar, gelatin, hydroxypropylcellulose, hydroxypropylmethyl cellulose phthalate, etc.) or with two or more layers. Furthermore, the solid preparation includes a capsule preparation with use of such an absorbable material as gelatin.

Examples of the liquid preparation for oral administration include pharmaceutically allowable aqueous solution, suspension, emulsion, syrup and elixir preparations, etc. In such liquid preparations, one or more active agents are dissolved, suspended or emulsified in a temporarily used diluent (e.g., purified water, ethanol, mixtures thereof, etc.). Furthermore, such a liquid preparation may comprise a wetting agent, suspending agent, emulsifier, sweetening agent, flavor, fragrance, preservative or buffer, etc.

In addition, a sustained-release preparation for oral administration is also useful. The gel-forming substance usable for such sustained-release preparation means any substances which, in swelling by soaking up a solvent, is capable of allowing their colloidal particles to be joined mutually and assuming the three-dimensional network structure to thereby form a jelly-like substance lacking in fluidity. From the standpoint of processing into pharmaceutical preparations, such substances are used mainly as a binder, thickening agent or sustained-release excipient, and use can be made of, for example, arabic gum, agar, polyvinylpyrolidone, sodium alginate, propylene glycol alginate, carboxyvinylpolymer, carboxymethylcellulose, sodium carboxymethylcellulose, guar gum, gelatin, hydroxypropyl methylcellulose, hydroxypropylcellulose, polyvinylalcohol, methylcellulose or hydroxymethyl methylcellulose. Among others, hydroxypropyl methylcellulose (hereinafter referred to briefly as "HPMC") is suitably used. HPMC is available in various types showing varied degrees of hydroxypropoxyl or methoxyl substitution and different viscosities. Suited is Metolose Type 60SH (HPMC2910) or 90SH(HPMC2208) having an average viscosity of 4000 cps.

The injectable solution for parenteral administration includes solutions, suspensions, emulsions and solid injections to be used after be dissolved or suspended in a solvent on the occasion of use. The injectable solutions are used by dissolving, suspending or emulsifying one or more active substances in a solvent. As such a solvent, there may be used distilled water for injection, physiological saline, vegetable oils, alcohols such as propylene glycol, polyethylene glycol and ethanol, etc., and combinations thereof. Such injectable solution may further comprise a stabilizer, dissolution aid (e.g., glutamic acid, aspartic acid, Polysolvate 80 (trade name) etc.), suspending agent, emulsifier, soothing agent, buffer or preservative, etc. These injectable solutions are prepared through sterilization or aseptic process at the final step. These can also be utilized as an aseptic solid preparation (e.g., there is prepared a lyophilizate, which, prior to its use, is dissolved in sterilized or aseptic distilled water for injection or other solvents).

The preparation for external application for parenteral administration may be exemplified by ointment, gel, cream, wet compress, paste, liniment, nebula, inhalant, spray, aerosol, eye drops, collunarium and the like. These preparations each contain one or more active substances and are prepared by any known methods or commonly used formulation.

The ointment is prepared by any known or commonly used formulations, for example, by triturating or dissolving one or more active substances in a base. The ointment base is selected from known or commonly used materials, and use is made of, for example, higher aliphatic acids or higher aliphatic acid esters (e.g., myristic acid, palmitic acid, stearic acid, oleic acid, myristates, palmitates, stearatesic, oleates, etc.), waxes (e.g., beeswax, whalewax, ceresin, etc.), surface active agents (e.g., polyoxyethylenealkylether phosphoric acid ester, etc.), higher alcohols (e.g., cetanol, stearyl alcohol, setostearyl alcohol, etc.), silicon oils (e.g., dimethyl polysiloxane, etc.), hydrocarbons (e.g., hydrophilic petrolatum, white petrolatum, purified lanolin, liquid paraffin, etc.), glycols (e.g., ethylene glycol, diethylene glycol, propylene glycol, polyethylene glycol, macrogol, etc.), vegetable oils (e.g., castor oil, olive oil, sesame oil, turpentine oil, etc.), animal oils (mink oil, vitelline oil, squalane, squalene, etc.), water, absorption accelerators and skin-rash preventives, either singly or in admixture of two or more thereof. The base may further comprise a humectant, preservative, stabilizer, antioxidant or perfume, etc.

The gel is prepared by any known or commonly used formulations. For example, the gel is prepared by dissolving one or more active substances in a base. The gel base is selected from the known or commonly used materials, and use is made of, for example, lower alcohols (e.g., ethanol, isopropyl alcohol, etc.), gelling agents (e.g., carboxymethyl cellulose, hydroxyethyl cellulose, hydroxypropyl cellulose, ethyl cellulose, etc.), neutralizing agents (e.g., triethanolamine, diisopropanolamine, etc.), surface active agents (e.g., polyethylene glycol monostearate, etc.), gums, water, absorption accelerators, and skin-rash preventives, either singly or in admixture of two or more kinds thereof. The gel base may further comprise a preservative, antioxidant or perfume, etc.

The cream is prepared by any known or commonly used formulation, and is prepared, for example, by dissolving one or more active substances in a base. The cream base is selected from the known or commonly used materials, and use is made of, for example, higher aliphatic acid esters, lower alcohols, hydrocarbons, polyhydric alcohols (e.g., propylene glycol, 1,3-butylene glycol, etc.), higher alcohols (e.g., 2-hexyl decanol, cetanol, etc.), emulsifiers (e.g., polyoxyethylene alkyl ethers, aliphatic acid esters, etc.), water, absorption accelerators, and skin-rash preventives, either singly or in admixture of two or more kinds thereof. The cream base may further comprise a preservative, antioxidant or perfume, etc.

The wet compress is prepared by any known or commonly used formulations, and is prepared, for example, by melting one or more active substances in a base, and then applying and spreading the kneaded material over a support. The wet compress base is selected from the known or commonly used materials, and use is made of, for example, thickening agents (e.g., polyacrylic acid, polyvinyl pyrrolidone, gum arabic, starch, gelatin, methyl cellulose, etc.), wetting agents (e.g., urea, glycerin, propylene glycol, etc.), fillers (e.g., kaolin, zinc oxide, talc, calcium, magnesium, etc.), water, dissolution aids, tackifiers, and skin-rash preventives, either singly or in admixture of two or more kinds thereof. The wet compress base may further comprise a preservative, antioxidant, or perfume, etc.

The pasting preparation is prepared by any known or commonly used formulations, and is prepared, for example, by melting one or more active substances in a base and then applying and spreading the kneaded material over a support. The base for the pasting agent is selected from the known or commonly used materials, and use is made of, for example, polymer bases, fats and oils, higher aliphatic acids, tackifiers and skin-rash preventives, either singly or in admixture of two or more kinds thereof. The base for the pasting agent may further comprise a preservative, antioxidant or perfume, etc.

The liniment is prepared by any known or commonly used preparation, and is prepared, for example, by dissolving, suspending or emulsifying one or more active substances in a single one or not less than two kinds selected from water, alcohols (e.g., ethanol, polyethylene glycol, etc.), higher aliphatic acids, glycerol, soaps, emulsifiers, suspending agents, etc. The liniment may further comprise a preservative, antioxidant or perfume, etc.

The nebula, inhalant, spray and aerozol each may comprise the commonly used diluents, as well as stabilizers, such as sodium hydrogen sulfite and buffers capable of providing isotonicity, such as isotonic agents, inclusive of sodium chloride, sodium citrate, or citric acid, etc. The process for preparation of a spray is described in detail, for example, in U.S. Pat. Nos. 2,868,691 and 3,095,355.

The inhalant for parenteral administration may be exemplified by aerosols, powders for inhalation or solutions for inhalation, and the solutions for inhalation may be in the form of being used after dissolution or suspension in water or other suitable medium on the occasion of use.

These inhalants are prepared in accordance with the known method.

For example, the liquid for inhalation is prepared by appropriately selecting preservatives (e.g., benzalconium chloride, Parabens, etc.), colorants, buffering agents (e.g., sodium phosphate, sodium acetate, etc.), isotonic agents (e.g., sodium chloride, concentrated glycerol, etc.), thickening agents (e.g., carboxyvinyl polymers, etc.), absorption accelerators, etc., as the case may be.

The powder for inhalation is prepared by appropriately selecting lubricants (e.g., stearic acid and salts thereof, etc.), binders (e.g., starch, dextrin, etc.), vehicles (e.g., lactose, cellulose, etc.), colorants, preservatives (e.g., benzalconium chloride, Parabens, etc.), absorption accelerators, etc., if required.

In order to administer a patient the liquid for inhalation, a sprayer (e.g., atomizer, nebulizer etc.) is normally used. In order to administer a patient the powder for inhalation, a powder inhaler is normally used.

Other examples of the compositions for parenteral administration include a suppository for rectal application and pessary for vaginal application which comprise one or more active substances and prepared by the ordinary method.

EXAMPLES

Examples

The present invention is to be described below by way of Examples and Biological Experiment Examples, but is not understood to be limited thereto.

Example 1

On the day of initiation of administration (Day 1 of Administration), the obese/spontaneously type II diabetic mice; KK-$A^y$/Ta Jcl mice (male, 6-weeks aged, n=8) were treated through individual oral administration of the Test Compound 1 (ethyl N-allyl-N—[(E)-2-methyl-3-[4-(4-amidinophenoxycarbonyl)-phenyl]propenoyl]aminoacetate/methanesulfonate) of the present invention and the Control Compound 1 (5-{4-[2-(5-ethylpyridine-2-yl)ethoxy]benzyl}-1,3-thiazolidine-2,4-dione; pioglitazone) at the daily dose of 30 mg/kg, or the control medium (0.5% CMC), and blood was drawn from each animal through the orbital venous plexus 6 hours after administration. The blood-sugar levels were measured in accordance with the enzyme electrode method by use of Antosense II (manufactured by Daikin Kogyo KK of Japan). The said test was carried out while the animals were allowed free access to food and water.

Following the above-described single administration, the repeated, once-a-day forced oral administration of each compound was performed at the same daily dose for the total period of 14 consecutive days. On Days 3 and 11, blood was drawn in the same manner as described above 6 hours after administration of each compound, followed by measurement of the blood-sugar level.

As from Day 14 afterwards, the animals after being fasted for 18 hours or more were loaded orally with a glucose solution (2 g/kg, 10 mL/kg), whereby the blood-sugar levels were measured before, and 120 min. after, the said glucose loading. Each of the compounds was given orally to the animals 3 hours prior to the glucose loading, and the whole blood was drawn from each of the animals under anesthesia. Each of the said blood samples was centrifuged to yield a blood plasma, and the resultant blood plasmas were all preserved under freezing in a ultra-low-temperature freezer for subsequent use in the below-described measurements.

The blood-sugar level, total cholesterol level (hereinafter referred to briefly as "TC level") and triglyceride level (hereinafter referred to briefly as "TG level") were detected individually in accordance with the hexokinase/G-6-PDH method, enzyme method and GPO/HDAOS method, and measured with use of Biochemical Auto-Analyzer (Model AU 400, manufactured by Olympus Co. of Japan). The plasma insulin level (hereinafter referred to briefly as "IRI level") and the plasma glucagon level (hereinafter referred to briefly as "IRG level") were detected individually with the ELISA method (Lebisinsulin Mouse Insulin Kit, produced by K.K. Shibayagi of Japan) and the ELISA method (YK090 Glucagon EIA Kit, produced by K.K. Yanaihara Kenkyuusho of Japan), followed by measurement with use of a plate reader (Immuno Mini NJ-2300, Nalge Nunc International K.K. of Japan).

The blood-sugar, TC, TG, IRI and IRG levels and the body weight were expressed as a mean value±standard deviation as calculated for each group of animals. With reference to the significance test between the group treated through administration of the medium and each group treated through administration of the compound, the F test was effected to analyze the data and then, the Student's t-test and Aspin-Welch's t-test were used in cases where the variance between the two groups was determined to be equal and unequal, respectively. Referring to the significance level, less than 5% (p<0.05) was considered significant, and the significance level was expressed as divided into the two events of less than 1% (**: p<0.01) and less than 5% (*: p<0.05).

[Results]

Table 1 tabulates the effects on the blood-sugar levels of each compound through single administration. As is obvious from the table, the Test Compound 1 exhibited a significant blood-sugar lowering action 6 hours after administration, as compared with the control medium group, while, on the other hand, the Control Compound 1 failed to elicit any significant blood-sugar lowering action.

Table 2 tabulates the effects of each compound on the blood-sugar levels at Days 3 and 11 after repeated administration. As is obvious from the table, the Test Compound 1 through repeatedly administration exhibited a blood-sugar lowering action Table 3 presents the effects of each compound on the blood-sugar levels as determined in the glucose loading test after repeated administration for 14 consecutive days. As is obvious from the table, the Test Compound 1 exhibited a significant blood-sugar lowering action, as compared with the medium control group, whereas the Control Compound 1 was not observed to produce any significant difference.

Table 4 tabulates the effects of each compound on the TC and TG levels as determined 3 hours subsequent to the glucose-loading test after repeated administration for 14 consecutive days. As is obvious from the table, the Test Compound 1 showed decreases individually in the TC and TG levels.

Table 5 tabulates the effects of each compound on the blood-sugar, plasma insulin (IRI) and plasma glucagon (IRG) levels as determined 3 hours subsequent to the glucose-loading test after repeated administration for 14 consecutive days. As is obvious from the table, the Test Compound 1 showed individually a decrease in the blood-sugar level, an increase in the IRI level and a decrease in the IRG level.

Table 6 presents the effects of each compound on the mouse body-weight after repeated administration for 14 consecutive days. As is obvious from the table, the Test Compound 1 did not show any changes in the mouse body-weight, as compared with the control medium group, whereas the Control Compound 1 displayed a significant elevation in the body weight.

The Test Compound 1 through repeated forced oral administration, ameliorated impaired glucose tolerance in the spontaneously diabetic mice, while it exhibited blood-sugar and blood-lipid lowering actions. In the meanwhile, such actions were interpreted to be attributed to the plasma-insulin level increasing and plasma-glucagon level lowering actions of the Test Compound 1, whereas the said compound was not observed to exhibit a body-weight elevating action.

TABLE 1

|  | Before administration (mg/dL) | 6 hrs. after administration |
|---|---|---|
| Control medium | 441.9 ± 19.9 | 321.9 ± 22.6 |
| Test Compound 1 | 443.5 ± 19.6 | 263.5 ± 11.0* |
| Control Compound 1 | 440.6 ± 24.3 | 287.9 ± 28.6 |

TABLE 2

|  | Day 3 (mg/dL) | Day 11 |
|---|---|---|
| Control medium | 286.0 ± 26.2 | 331.4 ± 33.3 |
| Test Compound 1 | 205.5 ± 7.0* | 297.4 ± 18.4 |
| Control Compound 1 | 224.4 ± 14.4 | 220.3 ± 8.2* |

TABLE 3

|  | Before glucose loading (mg/dL) | 120 Min. after glucose loading |
|---|---|---|
| Control medium | 156.3 ± 7.6 | 285.8 ± 20.9 |
| Test Compound 1 | 155.0 ± 5.2 | 235.0 ± 5.9* |
| Control Compound 1 | 156.9 ± 5.3 | 236.9 ± 19.6 |

TABLE 4

|  | TC (mg/dL) | TG (mg/dL) |
|---|---|---|
| Control medium | 110.8 ± 5.2 | 87.6 ± 6.7 |
| Test Compound 1 | 99.2 ± 3.6 | 81.4 ± 7.1 |
| Control Compound 1 | 114.6 ± 4.8 | 72.7 ± 4.7 |

TABLE 5

|  | Blood-sugar level (mg/dL) | IRI (ng/mL) | IRG (ng/mL) |
|---|---|---|---|
| Control medium | 288.3 ± 22.3 | 1.19 ± 0.33 | 501.3 ± 43.0 |
| Test Compound 1 | 251.0 ± 7.2 | 1.74 ± 0.17 | 410.7 ± 31.5 |
| Control Compound 1 | 289.9 ± 20.6 | 1.25 ± 0.28 | 487.7 ± 45.8 |

TABLE 6

|  | Body weight (g) |
|---|---|
| Control medium | 29.5 ± 0.5 |
| Test Compound 1 | 29.3 ± 0.3 |
| Control Compound 1 | 31.7 ± 0.8* |

Example 2

KK-A$^y$/Ta Jcl Mice (male, 6- to 7-weeks aged, the number of cases; 8 animals) were treated through individual administration, in the form of an admixture with a food, of the Test Compound 2 (N-allyl-N-{(2E)-3-[4-({4-[amino(imino)methyl]phenoxy}-carbonyl)phenyl]-2-methyl-2-propenoyl}glycine/dimethane-sulfonate) of the present invention and the Control Compound 1 (5-(4-[2-(5-ethylpyridine-2-yl)ethoxy]benzyl)-1,3-thiazolidine-2,4-dione; pioglitazone) at the daily dose of 16.8 mg/100 g-food for 7 consecutive days, whereby the control group was fed with an ordinary food alone.

Blood was drawn from the tail vein individually on the day (Day 1) preceding to administration of the Test Compound in the form of an admixture with a food, and on Days 2, 5, 7 and 14 of administration, and the blood samples were subjected to measurement of the blood-sugar level in accordance with the same procedure as described in Example 1, while, at the same time, the animals were weighed.

[Results]

Table 7 tabulates the effects of each compound on the blood-sugar levels through consecutive administration in the form of an admixture with a food. The Test Compound 2 was found to exhibit, as from Day 5 afterwards, a significant blood-sugar lowering action, which exceeded the one produced by the Control Compound 1. Table 8 shows time-course changes in the body weights, and the Control Compound 1 displayed the tendency to elevate the body weight, whereas the Test Compound 2 was not observed to produce any difference from the control group.

In conclusion, the Test Compound 2 through repeated administration in the form of an admixture with a food exhibited a more potent blood-sugar lowering action, as compared with the Control Compound 1, but did not show any body-weight elevating actions.

The blood samples taken from the tail vein on the respective specified days after the administration were subjected to measurement of the blood-sugar level in accordance with the method as described in Example 1, while the plasma glucagon level after the forced oral administration performed on Days 28 was measured in accordance with the ELISA method as described in Example 1. Also, the glycosylated hemoglobin (HbA1c) and GLP-1 levels were determined in accordance with the latex coagulation method and the ELISA method (YK160, GLP-1 EIA Kit, produced by K.K. Yanaihara Kenkyu-sho of Japan), respectively, while the TG level was measured in accordance with the method as described in Example 1. The total pancreatic insulin content

TABLE 7

| | Blood-sugar level (mg/dL) | | | | |
|---|---|---|---|---|---|
| | Day 1 | Day 2 | Day 5 | Day 7 | Day 14 |
| Control group | 306.5 ± 19.5 | 388.8 ± 28.1 | 509.5 ± 41.8 | 456.3 ± 54.1 | 446.8 ± 38.0 |
| Test Compound 2 | 300.0 ± 18.9 | 286.5 ± 58.3 | 314.8 ± 14.4** | 291.0 ± 5.1** | 248.0 ± 11.5** |
| Control Compound 1 | 309.3 ± 21.2 | 323.3 ± 15.7 | 350.0 ± 13.6* | 311.3 ± 19.4* | 270.5 ± 10.8** |

TABLE 8

| | Body weight (g) | | | | |
|---|---|---|---|---|---|
| | Day 1 | Day 2 | Day 5 | Day 7 | Day 14 |
| Control group | 30.0 ± 0.9 | 30.0 ± 1.0 | 32.1 ± 1.1 | 32.6 ± 1.2 | 35.4 ± 1.4 |
| Test Compound 2 | 30.6 ± 0.6 | 29.8 ± 0.7 | 30.6 ± 0.8 | 32.4 ± 1.0 | 34.6 ± 1.3 |
| Control Compound 1 | 29.8 ± 0.7 | 30.4 ± 0.7 | 33.3 ± 0.8* | 34.6 ± 0.6 | 39.4 ± 1.1 |

Example 3

KK-A$^y$/Ta Jcl Mice (male, 6-weeks aged, the number of cases; 8 animals) were treated through individual administration, in the form of an admixture with a food, of the Test Compound 2 (N-allyl-N-{(2E)-3-[4-({4-[amino(imino)methyl]phenoxy}-carbonyl)phenyl]-2-methyl-2-propenoyl}glycine/dimethanesulfonate) of the present invention at the daily doses of 0.56 mg, 1.68 mg, 5.6 mg and 16.8 mg/100 g-food, respectively, and the Control Compound 1 (5-{4-[2-(5-ethylpyridine-2-yl)-ethoxy]benzyl}-1,3-thiazolidine-2,4-dion; pioglitazone) at the daily doses of 5.6 mg and 16.8 mg/100 g-food, respectively, for 7 consecutive days, whereby the control group was fed with an ordinary food alone.

Blood was drawn from the tail vein individually on the day preceding to administration of each compound in the form of an admixture with a food, and on Days 6, 11, 16, 21 and 28 of administration.

On Day 28 of administration of each compound in the form of an admixture with a food, furthermore, each animal after blood had been drawn from the tail vein was treated through individual forced oral administration of the Test Compound 2 in the form of the solutions individually consisting of 0.2, 0.6, 2.0 and 6.0 mg/mL-0.5% CMC suspension in each 5 mL/kg portion, as well as the Control Compound 1 in the form of the solutions individually consisting of 2.0 and 6 mg/mL-0.5% CMC suspension in each 5 ml/kg portion, followed by blood drawing 30 min. later and autopsy to thereby measure the weights of the pancreas, liver and kidney, whereby the control group was treated through administration of the 0.5% CMC suspension in the same portion.

after oral administration of each compound was determined by adding 75% ethanol to the isolated pancreas as frozen, followed by homogenization, and collecting the insulin fraction through Sep-Pak (C18; WATER) treatment of the supernatant liquid produced by centrifugation, followed by determination with the ELIZA method.

Histopathological analysis of the pancreas (pathological analysis of the pancreatic Langerhans' islets (α-, β- and δ-cells) was carried out by embedding the tissue in paraffin, followed by thin slicing and respective staining through the Grimelius staining, Gomori's aldehyde-fuchsin staining and Hellman-Hellerstroem' staining.

[Results]

As is illustrated in FIG. 1 (□; 0.56 mg of the Test Compound 2/100 g of a food, Δ; 1.68 mg of the Test Compound 2/100 g of a food, X; 5.6 mg of the Test Compound 2/100 g of a food, *; 16.8 mg of the Test Compound 2/100 g of a food, ○; 5.6 mg of the Test Compound 1/100 g of a food, +; 16.8 mg of the Test Compound 1/100 g of a food, ◇ ; Control Group), the time-course changes in the blood-sugar level at satiety in the maximum-dosed (16.8 mg/100 g) group for the Test Compound 2 revealed significant continued drops in the blood-sugar level as from Day 6 of administration of the admixture afterwards, as compared with the Control Group, with such effect being found to last until the end of the test (Day 28), while in the intermediate-dosed group (5.6 mg/100 g), there was observed the tendency for the blood-sugar level to drop significantly as from Day 16 of administration afterwards, as well as a significant drop in the blood-sugar level at the end of the test (Day 28), as compared with the Control Group (Table 9). In the high-dosed group (16.8 mg/100 g) for the Control Compound 1, on the other hand, there were noticed significant drops in blood-sugar level on Days 6 and 11, but thereafter the blood-sugar level rose gradually, resulting in no blood-sugar lowering effect observed at the end of the test (Day 28) (Table 9).

Changes in plasma GLP-1 level 30 min. after forced oral administration made at the end of the test (Day 28) indicated that the plasma GLP-1 increasing effect can be produced through administration of the Test Compound 2 (Table 10), and this resulted in drops in the plasma glucagon level, leading to observation of the individually decreased blood-sugar, HbA1C and TG levels (Table 11).

Referring now to the weights of organs, the weight of the pancreas increased after administration of the Test Compound 2, but the weight each of the liver and kidney were suppressed from rising through administration of the Test Compound 2, whereas the Control Compound 1 acted to raise further the weight of the liver (Table 12).

Administration of the Test Compound 2 was not only found to bring about an increase in the total pancreatic insulin content (Table 13), but also observed to enlarge the Langerhans' cells of the pancreatic islets and to increase the number of pancreatic B-cells, as revealed by the postmortem findings, leading to the interpretation of such findings that the GLP-1 secretion accelerating action can cause the development of the pancreatic B-cell proliferation promoting and pancreatic B-cell function enhancing effects.

The Test Compound 2, in addition to the pancreatic B-cell proliferation promoting and pancreatic B-cell function enhancing effects due to its GLP-1 secretion accelerating action, exhibited excellent glucagon-level decreasing action as well as more potent blood-sugar lowering and lipid decreasing actions than the Control Compound 1, resulting in improvement of the diabetic conditions. In addition to such actions, the Test Compound 2 also possesses LTB4 antagonistic action and the like (The Official Gazette of JP Hei-8-143529 A), and is considered to be useful in the prevention and/or treatment or therapy of arteriosclerosis which is included in complications of diabetes mellitus (Arterioscler Thromb Vasc Biol., 24, 369-375 (2004)).

TABLE 9

| | Dose (g/100 g-food) | Blood-sugar level (mg/dL) |
|---|---|---|
| Control Group | 0 | 534.9 ± 58.8 |
| Test Compound 2 | 0.56 | 524.6 ± 47.3 |
| Test Compound 2 | 1.68 | 620.9 ± 79.6 |
| Test Compound 2 | 5.6 | 369.7 ± 39.6* |
| Test Compound 2 | 16.8 | 251.2 ± 34.7** |
| Control Compound 1 | 5.6 | 561.6 ± 28.2 |
| Control Compound 1 | 16.8 | 497.0 ± 26.8 |

TABLE 10

| | Dose (g/100 g-food) | GLP-1 level (ng/mL) |
|---|---|---|
| Control Group | 0 | 1.26 ± 0.17 |
| Test Compound 2 | 0.56 | 1.23 ± 0.17 |
| Test Compound 2 | 1.68 | 1.00 ± 0.19 |
| Test Compound 2 | 5.6 | 1.17 ± 0.13 |
| Test Compound 2 | 16.8 | 2.06 ± 0.32* |
| Control Compound 1 | 5.6 | 1.79 ± 0.23 |
| Control Compound 1 | 16.8 | 1.72 ± 0.19 |

TABLE 11

| | Dose (g/100 g-food) | Blood-sugar level (mg/dL) | HbA1c (%) | Glucagon (pg/mL) | TG (mg/mL) |
|---|---|---|---|---|---|
| Control group | 0 | 581.3 ± 24.0 | 6.1 ± 0.5 | 487.9 ± 56.9 | 109.1 ± 8.9 |
| Test Compound 2 | 0.56 | 518.2 ± 40.4 | 6.3 ± 0.4 | 451.2 ± 61.7 | 117.0 ± 9.5 |
| Test Compound 2 | 1.68 | 581.9 ± 47.6 | 6.6 ± 0.2 | 244.4 ± 45.8** | 119.0 ± 3.4 |
| Test Compound 2 | 5.6 | 406.3 ± 39.7** | 5.1 ± 0.4 | 211.1 ± 23.9** | 112.0 ± 8.3 |
| Test Compound 2 | 16.8 | 359.2 ± 33.0** | 3.0 ± 0.2** | 188.7 ± 38.5** | 154.9 ± 9.2** |
| Control Compound 1 | 5.6 | 555.7 ± 43.5 | 7.1 ± 0.5 | 531.5 ± 46.7 | 116.9 ± 12.9 |
| Control Compound 1 | 16.8 | 511.0 ± 44.0 | 5.5 ± 0.4 | 454.8 ± 30.9 | 109.2 ± 3.8 |

TABLE 12

| | Dose (g/100 g-food) | Weight (g) Liver | Kidney | Pancreas |
|---|---|---|---|---|
| Control group | 0 | 1.93 ± 0.07 | 0.48 ± 0.01 | 0.37 ± 0.01 |
| Test Compound 2 | 0.56 | 2.01 ± 0.08 | 0.47 ± 0.01 | 0.342 ± 0.01 |
| Test Compound 2 | 1.68 | 2.08 ± 0.07 | 0.49 ± 0.01 | 0.41 ± 0.02 |
| Test Compound 2 | 5.6 | 1.80 ± 0.10 | 0.46 ± 0.01 | 0.54 ± 0.03** |
| Test Compound 2 | 16.8 | 1.52 ± 0.06** | 0.41 ± 0.01** | 0.45 ± 0.03* |
| Control Compound 1 | 5.6 | 2.38 ± 0.09** | 0.49 ± 0.01 | 0.34 ± 0.00* |
| Control Compound 1 | 16.8 | 2.62 ± 0.11** | 0.49 ± 0.02 | 0.36 ± 0.01 |

TABLE 13

| | Dose (g/100 g-food) | Total pancreatic insulin content (µg) |
|---|---|---|
| Control group | 0 | 12.23 ± 1.43 |
| Test Compound 2 | 1.68 | 9.40 ± 2.24 |
| Test Compound 2 | 5.6 | 17.11 ± 2.76 |
| Test Compound 2 | 16.8 | 18.74 ± 2.55+ |
| Control Compound 1 | 16.8 | 10.43 ± 1.81 |

Pharmaceutical Preparation Example 1

In accordance with the conventional procedure, the below-described ingredients were mixed and then tableted through compression to give 10,000 tablets each containing 5 mg of the active ingredient.

TABLE 14

| | |
|---|---|
| Ethyl N-allyl-N-[(E)-2-methyl-3-[4-(4-amidinophenoxy-carbonyl)-phenyl]propenoyl]amino acetate•methanesulfonate or N-allyl-N-{(2E)-3-[4-({4-[amino(imino)methyl]phenoxy}carbonyl)-phenyl]-2-methyl-2-propenoyl}glycine dimethanesulfonate | 50 g |
| Carboxymethylcellulose calcium (disintegrant) | 20 g |
| Magnesium stearate (lubricant) | 10 g |
| Microcrystalline cellulose | 920 g |

Pharmaceutical Preparation Example 2

After mixing the below-described ingredients with the conventional procedure, the resultant solution was sterilized with the conventional method, and filled in the 5-mL portion into ampoules, followed by freeze-drying with the conventional method to obtain 10000 ampoules each containing 20 mg of the active ingredient.

TABLE 15

| | |
|---|---|
| Ethyl N-allyl-N-[(E)-2-methyl-3-[4-(4-amidinophenoxy-carbonyl)-phenyl]propenoyl]amino acetate•methanesulfonate or N-allyl-N-{(2E)-3-[4-({4-[amino(imino)methyl]phenoxy}carbonyl)-phenyl]-2-methyl-2-propenoyl}glycine dimethanesulfonate | 200 g |
| Mannitol | 20 g |
| Distilled water | 50 L |

INDUSTRIAL APPLICABILITY

The protease-inhibiting compound according to the present invention can be used as an active ingredient of a preventive and/or therapeutic agent for diabetes and/or complications of diabetes.

The invention claimed is:

1. A method for treatment for type II diabetes comprising administering an effective dose of a compound represented by the general formula (I):

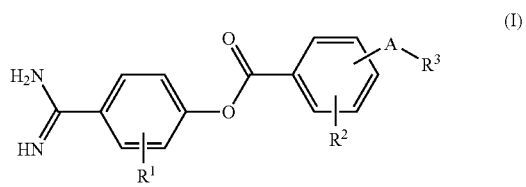

wherein $R^1$ and $R^2$ each independently are a hydrogen atom, a C1-4 alkyl, C1-4 alkoxy or C2-5 acyl group, a halogen atom, a nitro or benzoyl group, or $COOR^4$ (where $R^4$ is a C1-3 alkyl group);

A is a single bond, a C1-4 alkylene group, or a group represented by the formula:

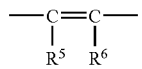

where $R^5$ and $R^6$ each independently are a hydrogen atom or a C1-4 alkyl group;

$R^3$ is a group represented by the general formula:

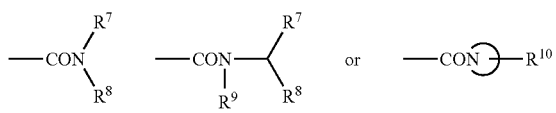

where $R^7$ and $R^8$ each independently are (1) a hydrogen atom, (2) a phenyl group, (3) a C7-10 phenylalkyl group, (4) a phenyl group substituted by one or more substituents selected from a C1-4 alkyl group, a halogen atom and $-R^{11}-COOR^{12}$ (where $R^{11}$ is a single bond, a C1-8 alkylene, C2-8 alkenylene or C2-8 alkynylene group; $R^{12}$ is a hydrogen atom, a C1-4 alkyl, C7-10 phenylalkyl, phenyl, aryl or propargyl group) or a C7-10 phenylalkyl group, (5) a C1-10 alkyl group, (6) a C2-10 alkenyl group having 1 to 3 double bonds, (7) a C2-10 alkynyl group having 1 to 2 triple bonds, (8) $-R^{11a}-COXR^{12}$ (where $R^{11a}$ is a single bond, a C1-8 alkylene group, a C2-8 alkylene group having one or two carbon atoms in the principal chain being substituted by a sulfur atom or a sulfur atom and a phenylene group, a C2-8 alkenylene group, a C4-8 alkenylene group having one or two carbon atoms in the principal chain being substituted by a sulfur atom, or a sulfur atom and a phenylene group, a C2-8 alkynylene group, or a C4-8 alkynylene group having one or two carbon atoms in the principal chain substituted by a sulfur atom or a sulfur atom and a phenylene group; X is an oxygen atom or NH; $R^{12}$ has the same meaning as described above), (9) a C1-4 alkyl group substituted by a 7-14 membered, bi- or tri-cyclic hetero ring containing one nitrogen atom, (10) a C3-7 cycloalkyl group or (11) a C1-6 alkyl group substituted by a C1-4 alkoxy group;

$R^9$ is (1) a hydrogen atom, (2) a C1-8 alkyl group, (3) a C7-10 phenylalkyl group, (4) a C2-10 alkenyl group having 1 to 3 double bonds, (5) a C2-10 alkynyl group having 1 to 2 triple bonds, (6) $-R^{11}-COOR^{12}$ (where $R^{11}$ and $R^{12}$ have the same meaning as described above), (7) a C3-7 cycloalkyl group, or (8) a C1-6 alkyl group substituted by a C1-4 alkoxy group;

the symbol:

is a 4-7 membered, mono-cyclic hetero ring containing one or two nitrogen atoms;

$R^{10}$ is (1) a hydrogen atom, (2) a C7-10 phenylalkyl group, or (3) $COOR^{13}$ (wherein, $R^{13}$ is a hydrogen atom, a C1-4 alkyl or C7-10 phenylalkyl group), with the proviso that $R^7$ and $R^8$ shall not represent a hydrogen atom at the same time and, when at least one group of $R^7$, $R^8$ and $R^9$ represents a group containing t-butyl ester, the other groups shall not represent a group containing carboxyl, or a salt thereof.

2. The method according to claim 1, wherein the compound represented by the general formula (I) is a compound represented by the formula:

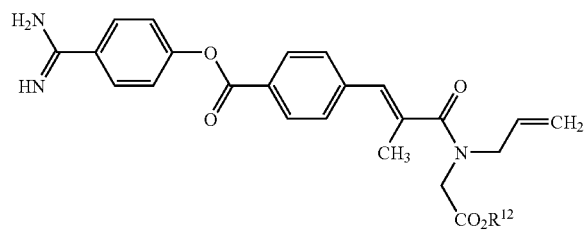

(I-1)

wherein $R^{12}$ is a hydrogen atom or a C1-4 alkyl group.

3. The method according to claim 2, wherein $R^{12}$ is a hydrogen atom or an ethyl group.

4. The method according to Claim 1, wherein the compound represented by the general formula (I) enhances GLP-1 generation.

5. The method according to Claim 1, wherein the compound represented by the general formula (I) decreases the amount of glucagon.

6. The method according to Claim 1, wherein the compound represented by the general formula (I) suppresses the elevation of blood sugar level and/or decreases blood-sugar level.

7. The method according to Claim 1, wherein the compound represented by the general formula (I) decreases lipid level.

8. The method according to Claim 1, wherein the compound represented by the general formula (I) promotes the regeneration of pancreatic beta-cells.

9. The method according to Claim 1, wherein the compound represented by the general formula (I) promotes insulin-synthesis.

10. The method according to Claim 1, wherein the compound represented by the general formula (I) is N-allyl-N—[(E)-2-methyl-3-[4-(4-amidinophenoxycarbonyl)-phenyl]-propenoyl]amino acetate or N-allyl-N-{(2E)-3-[4-({4-[amino(imino)methyl]phenoxy}carbonyl)-phenyl]-2-methyl-2-propenoyl}glycine, or a salt thereof.

* * * * *